US 6,712,836 B1

(12) United States Patent
Berg et al.

(10) Patent No.: US 6,712,836 B1
(45) Date of Patent: Mar. 30, 2004

(54) APPARATUS AND METHODS FOR CLOSING SEPTAL DEFECTS AND OCCLUDING BLOOD FLOW

(75) Inventors: Todd A. Berg, Plymouth, MN (US); Alex A. Peterson, Maple Grove, MN (US); William J. Swanson, St. Paul, MN (US); Paul J. Hindrichs, Plymouth, MN (US)

(73) Assignee: St. Jude Medical ATG, Inc., Maple Grove, MN (US)

( * ) Notice: Subject to any disclaimer, the term of this patent is extended or adjusted under 35 U.S.C. 154(b) by 0 days.

(21) Appl. No.: 09/570,358

(22) Filed: May 12, 2000

Related U.S. Application Data
(60) Provisional application No. 60/134,250, filed on May 13, 1999.

(51) Int. Cl.⁷ ............................................... A61B 17/04
(52) U.S. Cl. ..................................................... 606/213
(58) Field of Search ................................ 606/213, 139

(56) References Cited

U.S. PATENT DOCUMENTS

| 3,221,746 A | 12/1965 | Noble ........................ 606/151 |
| 3,657,744 A | 4/1972 | Ersek ........................ 606/153 |
| 4,214,587 A | 7/1980 | Sakura, Jr. ............... 128/334 R |
| 4,503,569 A | 3/1985 | Dotter ............................ 3/1.4 |
| 4,592,754 A | 6/1986 | Gupte et al. ................... 623/1 |
| 4,617,932 A | 10/1986 | Kornberg ................. 128/334 R |
| 4,665,906 A | 5/1987 | Jervis ...................... 128/92 YN |
| 4,733,665 A | 3/1988 | Palmaz ........................ 128/343 |
| 4,739,762 A | 4/1988 | Palmaz ........................ 128/343 |
| 4,787,899 A | 11/1988 | Lazarus ........................... 623/1 |
| 5,104,399 A | 4/1992 | Lazarus ........................... 623/1 |
| 5,122,156 A | 6/1992 | Granger et al. .............. 606/219 |
| 5,135,467 A | 8/1992 | Citron ............................ 600/16 |
| 5,147,370 A | 9/1992 | McNamara et al. ......... 606/108 |

(List continued on next page.)

FOREIGN PATENT DOCUMENTS

| AU | 670239 | 1/1994 | ............. A61F/2/06 |
| DE | 28 22 603 A1 | 11/1979 | ............. A61F/1/00 |
| DE | 195 42 733 A | 7/1997 | ............ A61B/17/11 |
| EP | 539237 | 4/1993 | ............. A61F/2/06 |

(List continued on next page.)

Primary Examiner—Gary Jackson
(74) Attorney, Agent, or Firm—Fish & Neave; Edward M. Arons

(57) ABSTRACT

Plugs and methods for plugging septal defects and blood vessels are provided. Plugs are delivered via catheter to a septal defect or a location where it is desired to occlude blood flow in a blood vessel. The plugs are positioned and expanded at the treatment site. The expansion of the plugs can be accomplished passively by using a heat-treated elastic frame or actively by using a balloon to deform a plastically-deforming frame. Plugging structures mounted to the frame span the defect or lumen and prevent blood flow. The plugs described herein have small profiles, and are more reliable than preceding intraluminal transcatheter methods.

153 Claims, 30 Drawing Sheets

U.S. PATENT DOCUMENTS

| | | | |
|---|---|---|---|
| 5,207,695 A | 5/1993 | Trout, III | 606/153 |
| 5,211,658 A | 5/1993 | Clouse | 623/1 |
| 5,211,683 A | 5/1993 | Maginot | 128/898 |
| 5,234,447 A | 8/1993 | Kaster et al. | 606/153 |
| 5,275,622 A | 1/1994 | Lazarus et al. | 623/1 |
| 5,304,220 A | 4/1994 | Maginot | 623/1 |
| 5,316,023 A | 5/1994 | Palmaz et al. | 128/898 |
| 5,334,217 A | 8/1994 | Das | 606/213 |
| 5,354,309 A | 10/1994 | Schnepp-Pesch et al. | 606/198 |
| 5,354,336 A | 10/1994 | Kelman et al. | 623/6 |
| 5,360,443 A | 11/1994 | Barone et al. | 623/1 |
| 5,387,235 A | 2/1995 | Chuter | 623/1 |
| 5,397,345 A | 3/1995 | Lazarus | 623/1 |
| 5,397,355 A | 3/1995 | Marin et al. | 623/12 |
| 5,433,727 A | 7/1995 | Sideris | 606/213 |
| 5,443,497 A | 8/1995 | Venbrux | 623/1 |
| 5,452,733 A | 9/1995 | Sterman et al. | 128/898 |
| 5,456,712 A | 10/1995 | Maginot | 623/1 |
| 5,489,295 A | 2/1996 | Piplani et al. | 623/1 |
| 5,496,365 A | 3/1996 | Sgro | 623/1 |
| 5,507,769 A | 4/1996 | Marin et al. | 606/198 |
| 5,522,880 A | 6/1996 | Barone et al. | 623/1 |
| 5,522,882 A | 6/1996 | Gaterud et al. | 623/1 |
| 5,545,214 A | 8/1996 | Stevens | 623/2 |
| 5,562,728 A | 10/1996 | Lazarus et al. | 623/1 |
| 5,617,878 A | 4/1997 | Taheri | 128/898 |
| 5,653,747 A | 8/1997 | Dereume | 623/1 |
| 5,676,670 A | 10/1997 | Kim | 606/108 |
| 5,681,336 A | 10/1997 | Clement et al. | 606/159 |
| 5,693,083 A | 12/1997 | Baker et al. | 623/1 |
| 5,695,504 A | 12/1997 | Gifford, III et al. | 606/153 |
| 5,741,297 A * | 4/1998 | Simon | 604/285 |
| 5,755,778 A | 5/1998 | Kleshinski | 623/1 |
| 5,840,064 A | 11/1998 | Liprie | 604/96 |
| 5,843,164 A | 12/1998 | Frantzen et al. | 623/1 |
| 5,843,170 A | 12/1998 | Ahn | 623/1 |
| 5,843,175 A | 12/1998 | Frantzen | 623/1 |
| 5,853,419 A | 12/1998 | Imran | 606/191 |
| 5,853,422 A | 12/1998 | Huebsch et al. | 606/213 |
| 5,879,366 A * | 3/1999 | Shaw et al. | 606/151 |
| 5,921,995 A | 7/1999 | Kleshinski | 606/153 |
| 5,922,022 A | 7/1999 | Nash et al. | 623/1 |
| 5,976,178 A | 11/1999 | Goldsteen et al. | 623/1 |
| 6,013,190 A | 1/2000 | Berg et al. | 216/34 |
| 6,026,814 A | 2/2000 | LaFontaine et al. | 128/898 |
| 6,035,856 A | 3/2000 | LaFontaine et al. | 128/898 |
| 6,036,702 A | 3/2000 | Bachinski et al. | 606/153 |
| 6,036,716 A | 3/2000 | Kruchinin et al. | 606/198 |
| 2001/0021872 A1 * | 5/2001 | Bailey et al. | 623/1.24 |

FOREIGN PATENT DOCUMENTS

| | | | | |
|---|---|---|---|---|
| EP | 0 541 063 A | 5/1993 | | A61B/17/00 |
| EP | 637454 | 2/1995 | | A61M/25/10 |
| EP | 680734 | 11/1995 | | A61F/2/06 |
| EP | 684022 | 11/1995 | | A61F/2/06 |
| EP | 0 701 800 A1 | 3/1996 | | A61F/2/06 |
| EP | 0 712 614 A1 | 5/1996 | | A61F/2/06 |
| EP | 0 732 088 A2 | 9/1996 | | A61F/2/06 |
| EP | 0 732 089 A2 | 9/1996 | | A61F/2/06 |
| GB | 489316 | 7/1938 | | |
| GB | 2269104 A | 2/1994 | | A61F/2/06 |
| WO | WO 89/08433 A1 | 9/1989 | | A61F/2/04 |
| WO | WO 93/00868 | 1/1993 | | A61F/2/06 |
| WO | WO 93/13712 A | 7/1993 | | A61B/17/00 |
| WO | WO 93/20757 A2 | 10/1993 | | A61B/17/11 |
| WO | WO 94/01056 A1 | 1/1994 | | A61F/2/04 |
| WO | WO 95/21592 A1 | 8/1995 | | A61F/2/06 |
| WO | WO 95/32757 A1 | 12/1995 | | A61M/29/00 |
| WO | WO 96/01591 | 1/1996 | | A61B/17/22 |
| WO | WO 96/01599 | 1/1996 | | A61F/2/06 |
| WO | WO 96/14808 A1 | 5/1996 | | A61F/2/02 |
| WO | WO 96/18361 | 6/1996 | | A61F/2/06 |
| WO | WO 96/22745 | 8/1996 | | A61F/2/06 |
| WO | WO 96/25897 A2 | 8/1996 | | A61F/2/06 |
| WO | WO 97/13463 | 4/1997 | | A61B/17/00 |
| WO | WO 97/13471 | 4/1997 | | A61B/19/00 |
| WO | WO 97/27898 | 8/1997 | | A61M/29/00 |
| WO | WO 97/41779 A1 | 11/1997 | | A61B/17/00 |
| WO | WO 98/01086 | 1/1998 | | A61F/2/04 |
| WO | WO 98/02099 | 1/1998 | | A61B/17/00 |
| WO | WO 98/03118 | 1/1998 | | A61B/17/11 |
| WO | WO 98/08462 A | 3/1998 | | |
| WO | WO 98/19629 A2 | 5/1998 | | A61F/2/06 |
| WO | WO 98/19629 A3 | 5/1998 | | A61F/2/06 |
| WO | WO 98/19631 A1 | 5/1998 | | A61F/2/06 |
| WO | WO 98/26732 A1 | 6/1998 | | A61F/2/06 |
| WO | WO 98/27868 A | 7/1998 | | A61B/17/00 |
| WO | WO 98/38939 A1 | 9/1998 | | A61B/19/00 |
| WO | WO 98/38941 A1 | 9/1998 | | A61B/19/00 |
| WO | WO 98/38942 A1 | 9/1998 | | A61B/19/00 |
| WO | WO 98/42262 | 10/1998 | | A61B/17/04 |
| WO | WO 98/55027 A2 | 12/1998 | | A61B/17/00 |
| WO | WO 99/07289 A1 | 2/1999 | | A61B/17/00 |
| WO | WO 99/38454 | 8/1999 | | A61F/2/06 |

* cited by examiner

APPARATUS AND METHODS FOR CLOSING SEPTAL DEFECTS AND OCCLUDING BLOOD FLOW

This claims the benefit of U.S. provisional patent application No. 60/134,250, filed May 13, 1999, which is hereby incorporated by reference in its entirety.

BACKGROUND OF THE INVENTION

This invention relates to apparatus and methods for closing intravascular defects and occluding blood flow. In particular, it relates to closing septal defects or holes found between the walls of the four heart chambers and occluding blood flow in sections of a patient's circulatory system.

The heart chambers include left and right atrial chambers in the upper portion and left and right ventricular chambers in the lower portion. Defects in these walls can be formed congenitally or can develop later in life. An atrial septal defect (hereinafter, "ASD") is found between the right and left atrium and a ventricular septal defect (hereinafter, "VSD") is found between the left and right ventricles. The defect allows blood to be shunted between the chambers, causing the heart's pumping action to be inefficient, and creating a risk of embolization (the circulation of an abnormal particle through the bloodstream).

A similar defect is the patent ductus. The patent ductus is a pre-birth opening between the aorta and the pulmonary artery. This opening usually closes naturally, but may remain open and cause oxygenated blood to flow back into the lungs. Another defects are the ductus arteriosis and the patent foramen ovale (hereinafter, "PFO"). At least fifty percent of stroke patients under 55 years old have a PFO.

Therapeutic treatment of these defects normally requires extensive surgery. For example, treatment typically requires open heart surgery, cardiopulmonary bypass, and stopping of the heart. During treatment, the defect is sewn shut by applying a thin patch over the hole. Less invasive methods for closure of these defects, such as intraluminal transcatheter approaches, for example, but provide unreliable delivery and deployment. A transcatheter apparatus has a large delivery profile that limits application of the method to young patients and makes it difficult to match the apparatus to the intracardiac or extracardiac cavity and can result in thrombosis, emboli, or dislodgement due to interference with blood flow.

It is also known that septal holes cause strokes by shunting clots from the right atrium to the left atrium. From the left atrium, a clot can go to the brain. Some holes are asymptomatic and should still be closed to prevent future stroke. Patients having asymptomatic defects would benefit from a low-invasive and reliable treatment apparatus and method.

In addition to the treatment of septal defects, it is often desirable to occlude blood flow in a section of the circulatory system. Occlusion can control internal bleeding and buffer pressure in the vicinity of an aneurysm.

Therefore, it would be desirable to provide apparatus and methods for treating septal defects, such as ASD, VSD, and PFO, that function at least as well as the proven surgical thin sewn patch, but which are less invasive.

It would also be desirable to provide reliable apparatus and methods for delivery of intraluminal transcatheters and deployment of septal defect devices and plugs.

It would be more desirable to provide these apparatus and methods such that the delivery profile is small and such that they can be used to treat patients of a wide range of ages.

It would be further desirable to provide septal defect devices and occluding plugs that can be properly matched to the intracardiac or extracardiac cavity.

It would be still further desirable to provide apparatus and methods for percutaneous delivery and deployment of occlusion devices for blocking blood flow in various sections of the circulatory system.

SUMMARY OF THE INVENTION

Therefore, it is an object of the invention to provide apparatus and methods for treating septal defects, such as ASD, VSD, and PFO, that function as well as the proven surgical thin sewn patch, but which are less invasive.

It is also an object of the invention to provide reliable apparatus and methods for delivery of intraluminal transcatheters and deployment of septal defect devices and plugs.

Additionally, it is an object of the invention to provide these apparatus and methods such that the delivery profile is small and such that they can be used to treat patients of having a wide range of ages.

It is a further object of the invention to provide septal defect devices and occluding plugs that can be properly matched to the intracardiac or extracardiac cavity.

It is a still further object of the invention to provide apparatus and methods for percutaneous delivery and deployment of occlusion devices for blocking blood flow in various sections of the circulatory system.

In accordance with one aspect of the present invention, a plug is provided for closing an aperture in a wall of a patient's body cavity. The plug includes: a frame that has a central axis; a first plurality of fingers configured to engage an interior surface of the body cavity wall; a second plurality of fingers that are attached to the first plurality and are configured to engage an exterior surface of the body cavity wall; and a plugging structure. The fingers can be positioned substantially circumferentially about the central axis. The plugging structure is attached to the frame and spans the aperture when the plug is in position. Furthermore, cross-sections of the frame that lie in a plane substantially perpendicular to the central axis are substantially discontinuous in order to enable the plug, and particularly the frame, to conform to the perimeter, or contour, of the aperture.

According to another aspect of the invention, a plug is provided that has a perforated tubular portion having a longitudinal passage. Any cross-section of the perforated tubular portion taken along a plane perpendicular to the passage is substantially discontinuous to allow confirmation of the portion to perimeter of the aperture. The plug has a plurality of fingers extending from each of the two axial ends of the perforated tubular portion. Preferably, any cross-section of the fingers taken along a plane perpendicular to the passage is also substantially discontinuous. The plug also has a plugging structure as described above.

In yet another aspect of the invention, an occlusive device is provided for occluding blood flow at a treatment site. This device is similar to the preceding plugs, but has fingers extending from only one axial end of the perforated tubular portion. During operation, these fingers anchor the device to the internal surface of a blood vessel.

According to still another aspect of the invention, methods for plugging an aperture in a wall of a patient's body cavity is provided. The method includes positioning a conformable plug in the aperture, conforming the plug to the aperture, and securing the plug in the aperture. It will be appreciated that the steps of conforming and securing could occur at the same time. Methods for occluding blood flow are also provided.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE PREFERRED EMBODIMENTS

Figure 1:
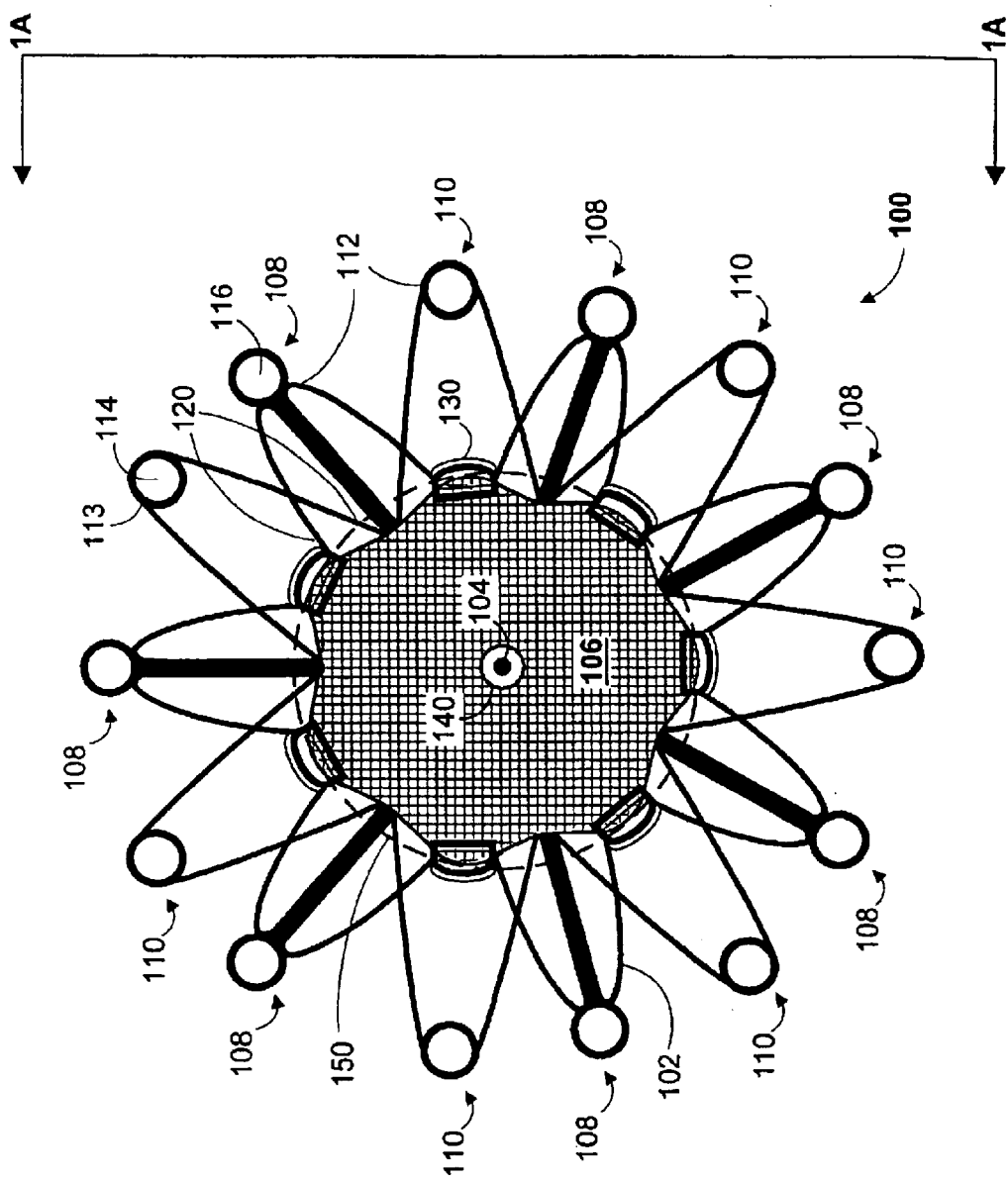
FIG. 1 is a plan view of a plug for plugging a septal defect in accordance with this invention.

The invention provides apparatus and methods for preventing the flow of body fluids through apertures in body cavity walls and through a patient's body tubing, such as a blood vessel. The apparatus can be a plug that is installed in the patient's body using an intraluminal catheter method. The plug can have a (1) frame that conforms to the walls of an aperture (e.g., a defect) or a section of tubing and (2) a plugging structure (e.g., a patch) that prevents the flow of fluid. Although the plug can be installed in a variety of types of body tissues to prevent the flow of body fluid, only embodiments of the invention related to preventing the flow of blood through passageways in the circulatory system will be illustrated herein.

In one embodiment, a plug is provided for closing an aperture or hole in a septal wall of a patient's heart, for example a PFO. The plug has a frame, two pluralities of fingers attached to axial ends of the frame and to each other, and a plugging structure attached thereto. The pluralities of fingers can be integral with the frame and formed from a unitary body. During operation, one plurality of fingers engages an interior surface of the wall and the other set of fingers engages the opposite, or exterior, surface. The plugging structure is supported by the frame and spans the aperture (e.g., defect) to prevent the flow of blood there through.

The fingers are preferably positioned substantially circumferentially (i.e., peripherally) about the plug's central axis, which passes through the frame. The fingers can extend radially away or along the axis. The fingers have ends that are radially proximal to the central axis and which generally define a substantially round or elliptical broken cross-section in a plane substantially perpendicular to the central axis.

Preferably, any cross section of the frame that lies in a plane substantially perpendicular to the axis is substantially discontinuous. This allows the frame to contract and expand radially as necessary for insertion into a delivery device, placement in an aperture, and confirmation to the walls of the aperture. The frame itself can comprise an elastic material, such as nitinol. Alternatively, the frame can comprise a plastically deforming material, such as stainless steel. The elastic and plastic embodiments may be delivered differently.

When the plug is inside the patient's body, medical scanners can be used to assist and confirm plug placement and to evaluate the integrity of a plug after it has been in use for an extended period of time. The frame may be equipped with one or more marker structures, which can be radiopaque, to help identify, locate, and orient the plug using images produced with, for example, X-rays, CT scans, ultrasound, and echo techniques Marker structures can be provided in a variety of forms. For example, a marker structure can be in the form of a marker band made from a radiopaque material that is crimped onto an end portion of a finger. Alternatively, a marker structure can be a rivet that is inserted and locked into a ring or hole in a finger. If marker structures are used, they can be provided on any number of fingers.

Other structures can be present on the fingers of the plug to facilitate its delivery. For example, a finger can be provided with a retention device receptacle. A retention device reciprocates within a delivery sleeve or catheter and engages the fingers while the plug is inserted in the delivery sleeve so that the plug can be reciprocated within the sleeve and shifted into position in the aperture, such as a PFO. Once in position, the retention device can release the fingers so that the fingers spring into engagement with the aperture wall.

In one embodiment, the frame of the plug is insertable into a delivery tube by extending the fingers in a direction substantially parallel to the central axis. The retention device itself has fingers or locking pins that engage the retention device receptacles that reside on the ends of the frame fingers. Retention device receptacle include, but are not limited to, locking pin apertures and nose cone covers.

Fingers may have a variety of designs that are tailored to optimize plug security for the shape and tissue characteristics of a given PFO. For example, fingers can have pointed ends, barbs, or curved portions. In one embodiment, fingers can be curved toward a plane that is perpendicular to the central axis and that passes substantially between the two pluralities of fingers. Fingers can be of substantially similar length or substantially different lengths. Any finger can have different flexural stiffness at different points along its length. One way to accomplish differential flexural stiffness of a finger is to provide a finger having a different thickness or a different width at different points along its length. Alternatively, both the finger thickness and the finger width can vary along the length of a given finger, if desired.

In certain cases, the force applied by a finger to the septum wall can be distributed to minimize stress concentration in the wall. In that case, the plug can be provided with an elastic web supported between adjacent fingers. The web, for example, can include silicone.

The plugging structure that occludes the PFO can be attached to or supported by the frame at proximal or distal ends of the fingers. In either case, the fingers' ends can be provided with support structures with which the plugging structure can be affixed.

In one embodiment, the plugging structure is made from an elastic material and can contract and expand as the frame contracts and expands (e.g., during delivery and deployment). One material that can be used to make the plugging structure is polyester (such as the material sold under the trademark DACRON® by E.I. du Pont de Nemours & Company of Wilmington, Del.).

The plugging structure can also be made from cloth and be folded and unfolded as the plug is contracted and expanded as may be necessary for its installation in the defect. In either the elastic or cloth embodiments of the plugging structure, the plugging structure can be attached (e.g., sewn) directly to the frame. The plugging structure can have a guide wire aperture through which a guide wire can pass. If the guide wire is inserted into the patient prior to plug delivery, the guide wire can be used to guide the plug into place in the PFO. The guide wire aperture can be designed to substantially self close after the guide wire is removed from the guide wire aperture. The self-closing feature can be achieved by making the diameter of a guide wire aperture in the relaxed state (i.e., without the wire) small enough to induce clotting and close off blood flow.

In another embodiment, the plug has a perforated tubular portion that forms a longitudinal passage. Fingers extend from each of the two axial ends of the perforated tubular portion and may be provided in a variety of configurations and made from a variety of materials. Any of the features discussed above may also be included. Like the frames discussed above, the perforated tubular portion is discontinuous along any cross section taken in a plane perpendicular to its longitudinal axis. This feature permits the perforated tubular portion to contract and expand radially and longitudinally for delivery, deployment, and confirmation to the walls adjacent a PFO, for example. Similarly, the plurality of fingers may be discontinuous along a cross section taken in a plane perpendicular to the longitudinal axis to allow such contraction and expansion as well.

The plugging structure can be supported directly or indirectly by the perforated tubular portion. For example, the plugging structure can be attached directly to the perforated tubular portion or to elements of the structure (such as tabs, bosses, extensions, or loops). Alternatively, the plugging structure can be attached via interceding support structures (such as attachment rings, clips, or loops) that connect the tubular portion to the plugging structure.

The perforated tubular portion preferably contracts longitudinally as it expands radially. The tubular portion can be made of a material that deforms plastically or elastically. A plastically deforming material can be, for example, stainless steel or tantalum. The plug is installed by positioning the plug in the aperture of the PFO and expanding a balloon inside the plug to at least partially conform the perforated tubular portion to the perimeter of the aperture. The perforations allow the plug to contract longitudinally in response to the radial expansion. The longitudinal contraction causes the fingers to engage opposing sides of the wall.

According to another aspect of the invention, an occlusion plug is provided. The occlusion plug has a perforated tubular portion for occluding a blood vessel. This type of plug may be desirable to prevent blood flow near a damaged portion of the vessel (e.g., aneurysm). The occlusion plug can be plastically or elastically deformable.

In the plastic embodiment, the occlusion plug is installed in the blood vessel by expanding a balloon in a longitudinal passageway of the perforated tubular portion. The expansion of the balloon causes the plug to expand radially and contract longitudinally. This expansion causes the outer surface of he perforated tubular portion to conform to the inner surface of the lumen of the blood vessel. The expansion also causes the fingers at the end of the perforated tubular portion to engage the inner surface of the wall as they are driven radially outward from the longitudinal axis and drawn longitudinally toward the perforated tubular portion.

The fingers of the occlusion plug preferably extend from only one axial end of the perforated tubular portion. The configuration of the fingers, the structures associated with the fingers, the perforated tubular portion, and the relation of the fingers to the perforated tubular portion are similar to those described above in connection with the PFO plug.

The invention also includes methods for preventing the flow of body fluids through apertures in body cavity walls. For simplicity plugging PFO's alone will be discussed. In a preferred embodiment, a plug that is at least partially made from an elastic material and is conformable to a defect, such as any of those elastic plugs described above having two opposing pluralities of fingers, is positioned at the defect, conformed to the perimeter of the defect and secured thereto.

In order to position the plug in the PFO, a delivery structure with a sleeve is provided. During the process of positioning the plug, the plug fingers are extended in a direction that is substantially parallel to the central axis of the plug while the plug is inserted into the sleeve of the delivery structure. A retention device inside the sleeve engages at least some of the extended fingers at the finger ends. The retention device can use locking pins, hooks, or any other means to retain the plug inside the sleeve. The retention elements permit an operator to reciprocate the plug longitudinally with respect to the sleeve and to shift the plug out from the end of the sleeve. The sleeve can be inserted like a catheter through an insertion aperture in a patient's body tissue. The sleeve can then be passed through the patient's internal body tubing or other body structures until the end of the sleeve is positioned within or adjacent the PFO for plug delivery.

Once the end of the sleeve is near or within the PFO, the delivery structure can be shifted relative to the plug and the PFO, thereby removing the delivery structure from the PFO. The plug, however, extends through the PFO and the plug fingers extend outward, preferably radially, from the central axis of the plug on opposite sides of the wall in which the PFO resides. This causes the plug fingers to engage the wall and the plugging structure to substantially occlude the PFO.

Preferably, releasing the plug within the PFO allows the plug to expand elastically inside the PFO until the plug substantially conforms to the inner rim or perimeter of the PFO. In one embodiment, the plug is allowed to elastically contract along the central axis of the plug while it expands radially. This longitudinal contraction causes the fingers to engage opposite sides of the same wall of the body cavity. A benefit of this approach is that the plug will center itself with respect to the wall in a direction along the plug's central axis (or along the longitudinal passage of the plug).

According to another embodiment of the invention, a plastically deformable plug can be inserted in a PFO using a balloon. A conformable plug, such as any of those plastically deformable plugs described above, is positioned in the PFO, conformed to the perimeter of the PFO, and then secured thereto. The positioning can be achieved by inserting a delivery balloon into the tubular portion of the plug and delivering both through a patient's body tissue, (e.g., through an insertion aperture and blood vessels), to the PFO. Then the balloon, which supports the plug, is moved through the patient's body until the plug is appropriately positioned in the aperture—such that one plurality of fingers is situated on each side of the wall.

The plug conforms to the PFO when the balloon is expanded. This causes the fingers to engage on both sides of the septal wall. The tubular portion of the plug radially enlarges and conforms to the perimeter of the aperture and the plugging structure occludes the aperture. When a plug (such as any of those described above) is used according to this method, the balloon expansion plastically deforms the tubular portion. This expansion automatically causes the tubular portion to contract in the direction parallel to the central axis of the plug. (It will be appreciated that the tubular portion could be annular or have a ring-like arrangement of tabs or other elements). The axial contraction causes the plug to substantially center itself with respect to the wall and drives the fingers into both sides of the wall.

A number of embodiments according to the present invention, with several variations, are shown in FIGS. 1–36.

FIG. 1 shows plug 100 for closing an aperture, such as an ASD, a VSD, or a PFO, in a wall of a patient's body cavity. Frame 102 can be made from an elastic material, such as nickel titanium (hereinafter, "nitinol," available, for example, from Shape Memory Applications, of Santa Clara, Calif.). The elastic nature of frame 102 allows frame 102 to radially contract sufficiently to allow it to be inserted into an aperture and subsequently radially expand to conform to the inner perimeter of the aperture. Other elastic materials can also be used to construct the frame and could be used in combination with other non-elastic materials. Radial expandability is facilitated by constructing the frame such that any cross section perpendicular to its central axis is discontinuous.

Frame 102 has central axis 104 and supports plugging structure 106. Frame 102 includes first plurality of fingers 108 and second plurality of fingers 110. In one embodiment, fingers 108 are integral with fingers 110. Fingers 108 and 110 have proximal ends 120 that are near central axis 104 and remote ends 112 that are near the radially outer portions of frame 102.

Proximal ends 120 can be used to support plugging structure 106 directly, or they can be equipped with support structures 130 for supporting plugging structure 106. Alternatively, remote ends 112 can support plugging structure 106. Remote ends 112 can also be equipped with support structures 113 for supporting plugging structure 106, and, as discussed more fully below, marker devices. The ends can also be adapted to engage a retention device during plug installation. In FIG. 1, each support structure 113 has aperture 114 to which a plugging structure can be sewn or otherwise attached.

Plugging structure 106 can be made from an elastic material. Plugging structure 106 can also be folded and unfolded to allow frame 102 to deform during insertion into the aperture. A foldable and unfoldable plugging structure can be either elastic or non-elastic and may include a cloth or polymeric material. In one embodiment, plugging structure 106 is made of polyester.

Plugging structure 106 can include guide wire aperture 140 for insertion of a guide wire (not shown) during installation of the plug in a patient. Guide wire aperture 140 may be self-closing after the removal of a guide wire. In elastic embodiments, the self closing feature may be effected by the elasticity of plugging structure 106. In cloth embodiments, which may or may not be elastic, the woven fibers under tension from frame 102 can automatically close guide wire aperture 140.

Remote ends 112 can also be provided with retention device receptacles for engaging a retention device that is part of a system for delivering the plug to an aperture in a wall. Finger aperture 114 can be used as a retention device receptacle. A nose cone cover (e.g., cover 314, shown in FIG. 3), is an alternative to a retention device receptacle. The delivery system is discussed below.

Figure 1A:
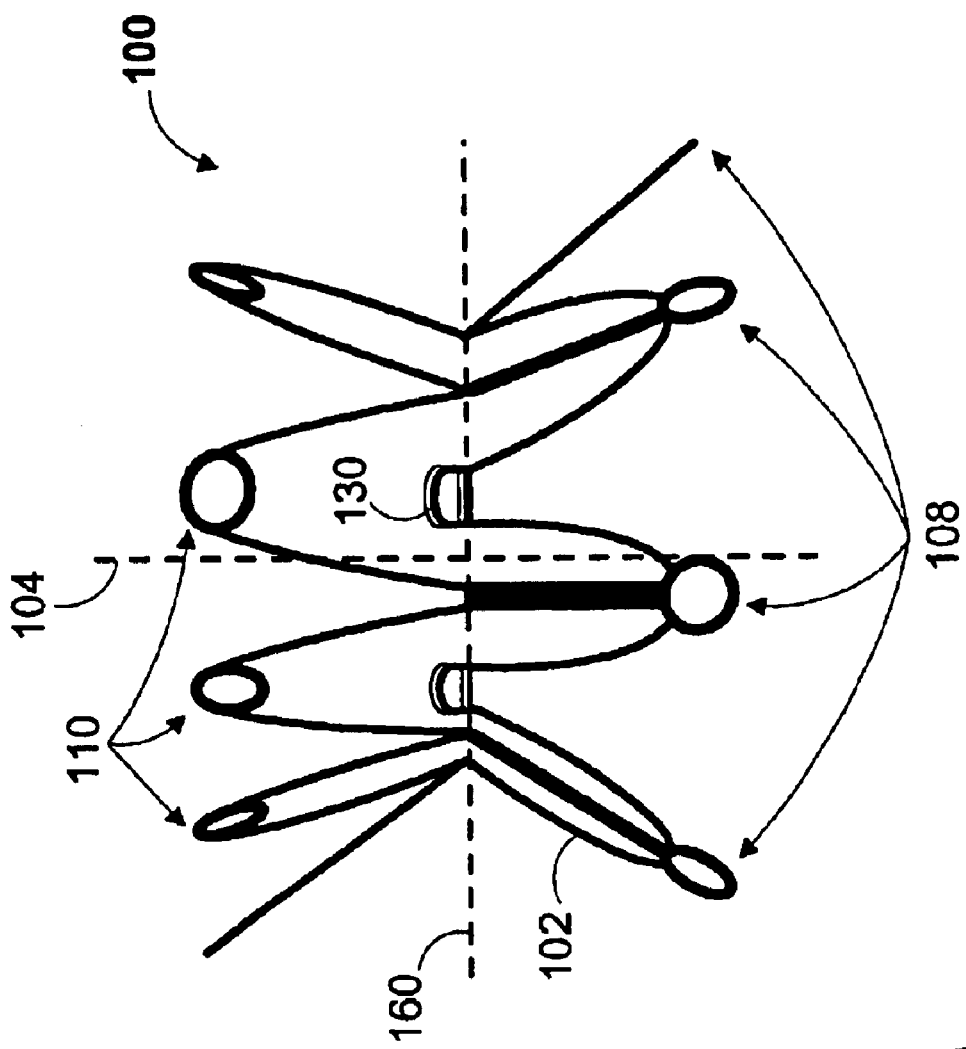
FIG. 1A is a partial side elevational view along direction 1A—1A of FIG. 1 in accordance with the principles of this invention.

As shown in FIG. 1, fingers 108 and 110 can extend substantially radially away from central axis 104, even though some of those fingers may have tangential or spiral components and may not conform to a radial pattern. One or more of fingers 108 and 110 may also contain marker structures, such as a marker band. FIG. 1A shows a partial side view of plug 100 with fingers 108 and 110 in an intermediate configuration without plugging structure 106. For illustrative purposes, only a small number of fingers are shown in FIG. 1A. In an intermediate configuration, fingers are neither parallel nor perpendicular to central axis 104. As can be seen from FIG. 1A, cross-section 160, which is perpendicular to central axis 104 and passes through the medial section of plug 100, is discontinuous.

Figure 2:
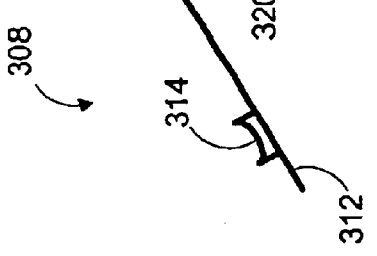
FIG. 2 is a side elevational view of a finger of a plug in accordance with this invention.
Figure 3:
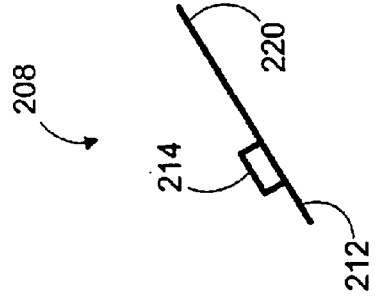
FIG. 3 is a side elevational view of another finger of a plug in accordance with this invention.
Figure 4:
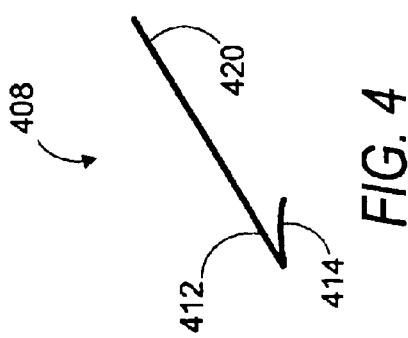
FIG. 4 is a side elevational view of yet another finger of a plug in accordance with this invention.
Figure 5:
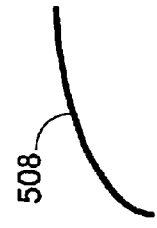
FIG. 5 is a side elevational view of still another finger of a plug in accordance with this invention.

FIGS. 2–5 show different features that can be incorporated into a finger. FIG. 2, for example, shows a side view of finger 208, having proximal end 220 and remote end 212, with rivet 214 mounted thereto. Rivet 214 can be mounted on a finger such that the rivet head engages the patient's heart wall or such that they face toward the heart cavity. FIG. 3 shows finger 308, having proximal end 320 and distal end 312, with nose cone cover 314. FIG. 4 shows finger 408, having proximal end 420 and distal end 412, with barb 414. FIG. 5 shows finger 508 which is curved. If a plug has two sets of fingers (as shown in FIG. 1), the fingers of each set may be curved toward each other.

Figure 6:
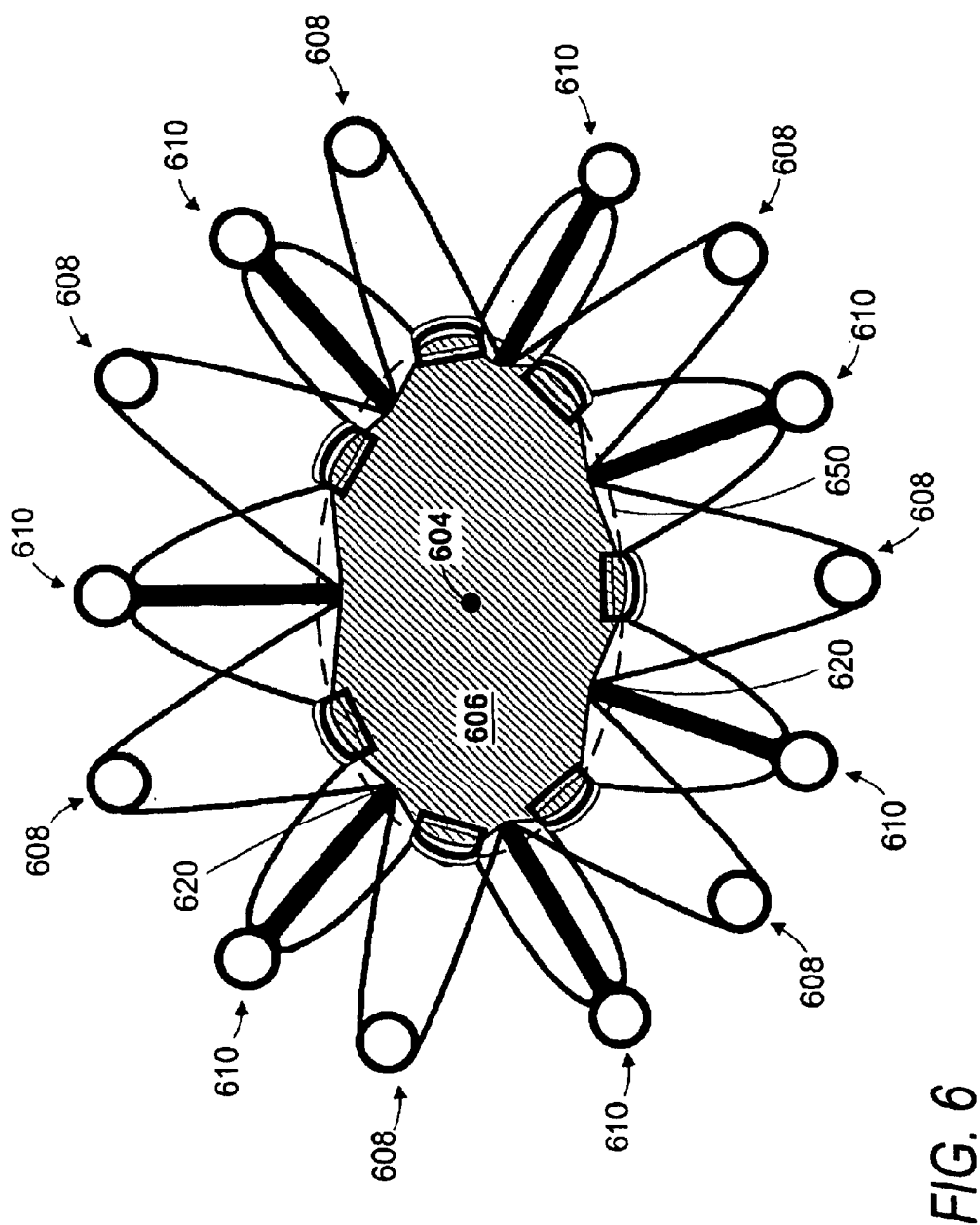
FIG. 6 is a plan view of another plug for plugging a septal defect in accordance with this invention.

FIG. 6 shows another embodiment of a plug constructed in accordance with this invention in which proximal ends 620 of fingers 608 and 610 define substantially elliptical cross section 650. Elliptical cross-section 650 is in contrast to round cross-section 150 shown in FIG. 1. As shown in FIG. 6, central axis 604 passes near the center point of the ellipse. plugging structure 606, which is supported by proximal ends 620, has a substantially elliptical shape and could have a guide wire aperture (not shown), if desired.

Figure 7:
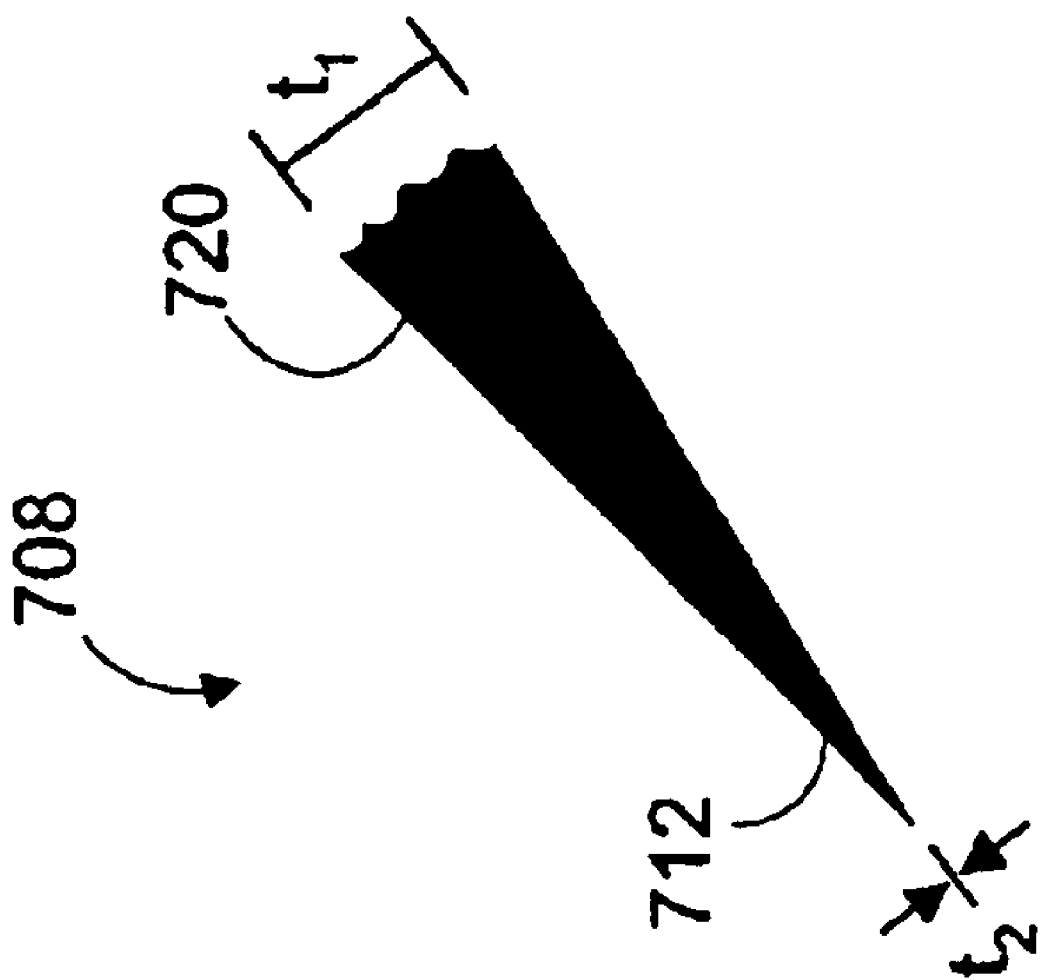
FIG. 7 is a side elevational view of yet another finger of a plug in accordance with this invention.

FIG. 7 shows an example of finger 708, which has proximal end 720 and distal end 712. Finger 708 tapers from thickness $t_1$ at proximal end 720 to lesser thickness $t_2$ at end 712 (e.g., remote from the plug's central axis). Conversely, finger 708 may be thicker at the remote end and thinner at the proximal end. Thus, a finger, such as finger 708, can have a resulting flexural stiffness that varies along its length. Fingers of varying width, such as the fingers shown in FIG. 1, can also have flexural stiffnesses that vary along their lengths regardless of variations in thickness by varying composition along the length.

Figure 8:
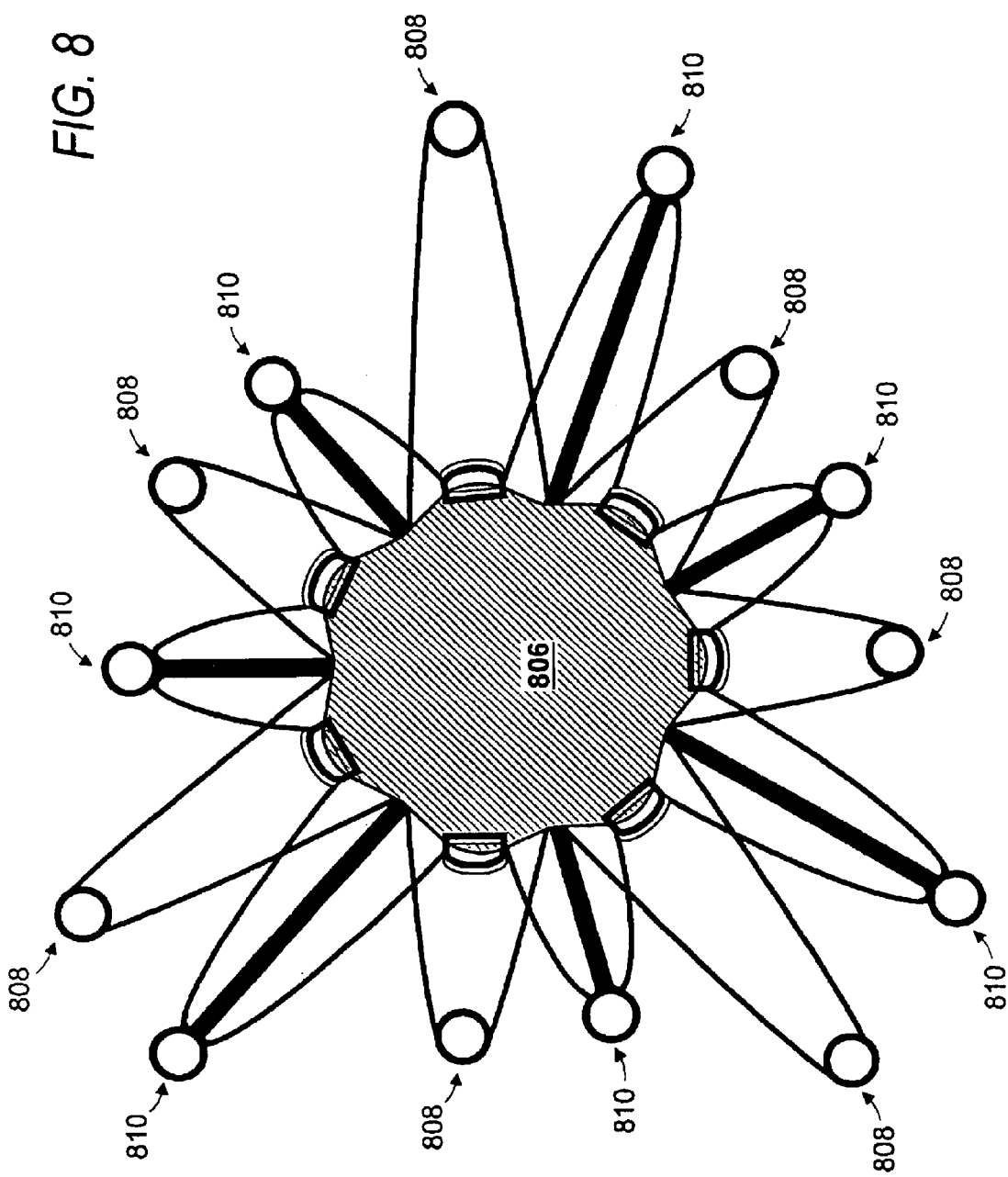
FIG. 8 is a plan view of yet another plug for plugging a septal defect in accordance with this invention.

FIG. 8 shows another illustrative embodiment of a plug constructed according to this invention in which fingers 808 and 810 have lengths that vary with respect to each other. Although fingers 808 and 810 have different lengths, it will be appreciated that plugging structure 806 can have a substantially circular, or any other convenient, shape.

Figure 9:
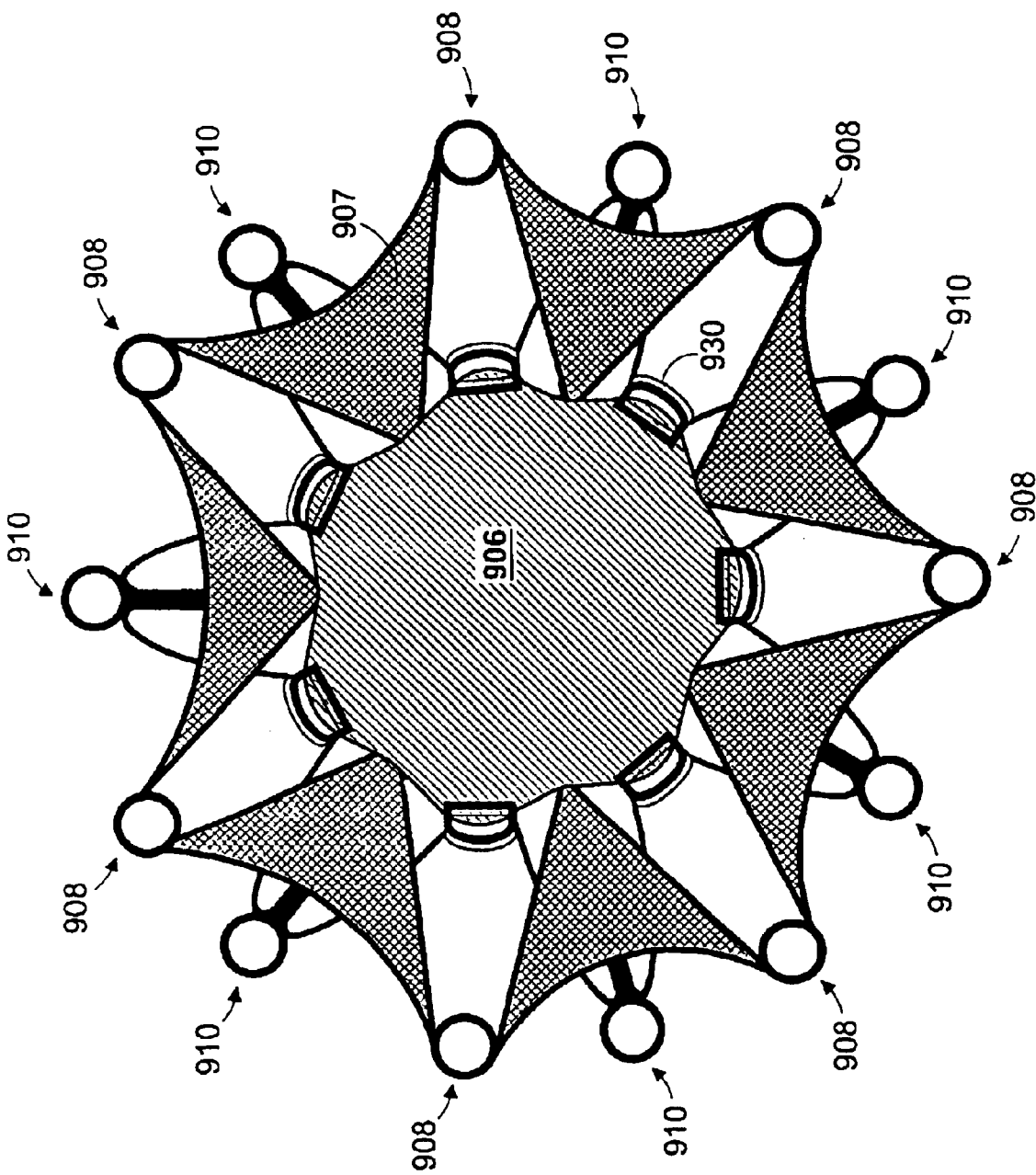
FIG. 9 is a plan view of yet another plug for plugging a septal defect in accordance with this invention.

FIG. 9 shows another alternative embodiment of a plug constructed according to this invention in which elastic web 907 spans between adjacent fingers of a plurality of fingers 908. The web can be made from any elastic material, including silicone. Plugging structure 906 is supported by proximal ends of fingers 908 and 910, and can be supported by support structures 930.

Figure 10:
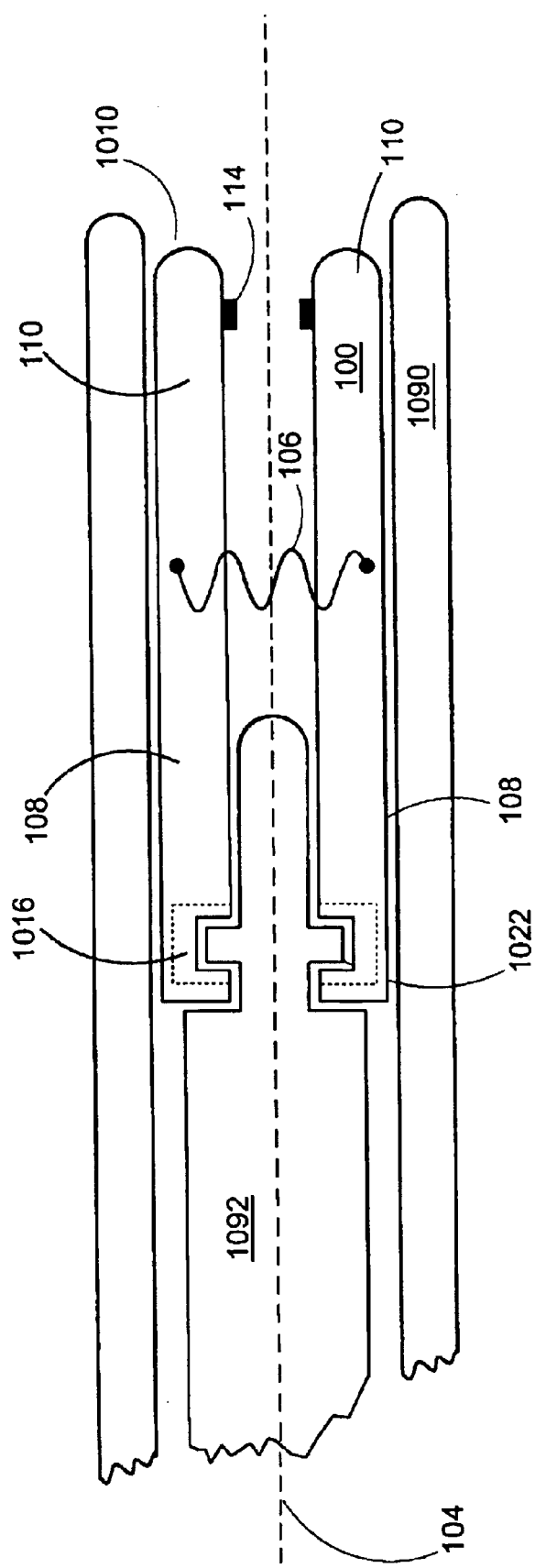
FIG. 10 is a cross-sectional view of a plug for plugging a septal defect disposed within a delivery device in accordance with this invention.

FIG. 10 shows how a plug, such as plug 100, can be installed via a delivery device, such as delivery catheter 1090. Plug 100 is inserted into delivery catheter 1090 by orienting fingers 108 and 110 in a direction that is substantially parallel to central axis 104. Next, plug 100 is passed through to distal opening 1010. Optional marker rivets 114 are shown in FIG. 10. Although it will be appreciated that plugging structure 1006 can be any convenient type, plugging structure 1006 is shown as a folded plugging structure. Retention device receptacles 1016 are engaged with locking pins 1022 of retention device 1092.

Figure 11:
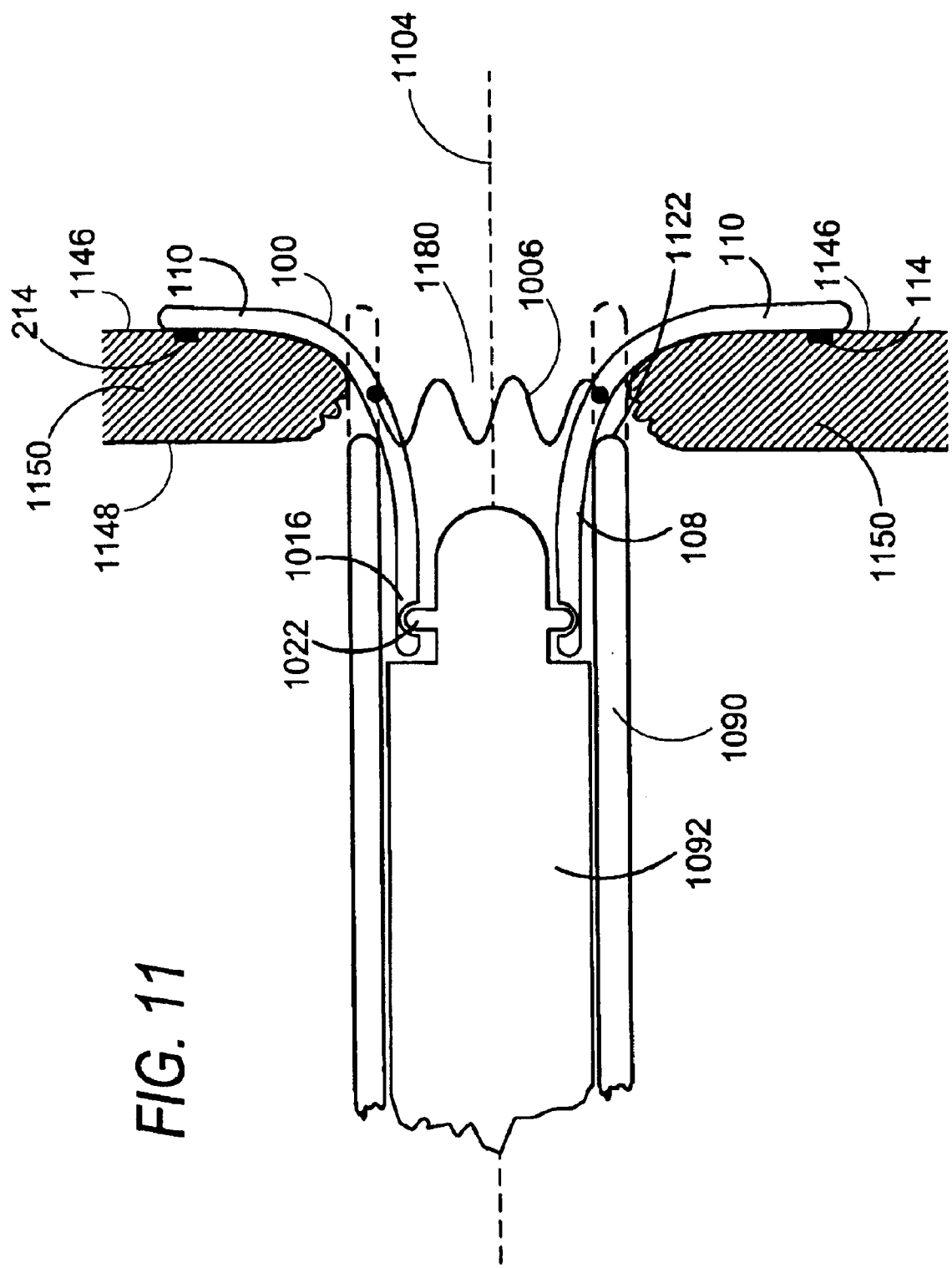
FIG. 11 is a cross-sectional view of the plug shown in FIG. 10 when the plug is partially deployed in the septal defect in accordance with this invention.

Once plug 100 is positioned near distal opening 1010, plug 100 can be inserted into aperture 1180 in wall 1150 of a patient's body cavity, as shown in FIG. 11. Initially, end 1122 of delivery catheter 1090 is positioned within aperture 1180 (indicated by a dashed line). Delivery catheter 1090 is then partially reciprocated away from aperture 1180 along axis 1104 and with respect to retention device 1092 (indicated by solid line). This forces fingers 110 out of delivery catheter 1090 and causes fingers 110 to spring out radially away from central axis 1104, thereby causing fingers 110 to engage side 1146 of wall 1150. At this stage, fingers 110 conform to the wall and perimeter of aperture 1180. Although FIG. 11 shows markers 114 attached to fingers 110 so they face wall 1050, it will be appreciated that these markers could also be located on the opposite side of these fingers.

Figure 12:
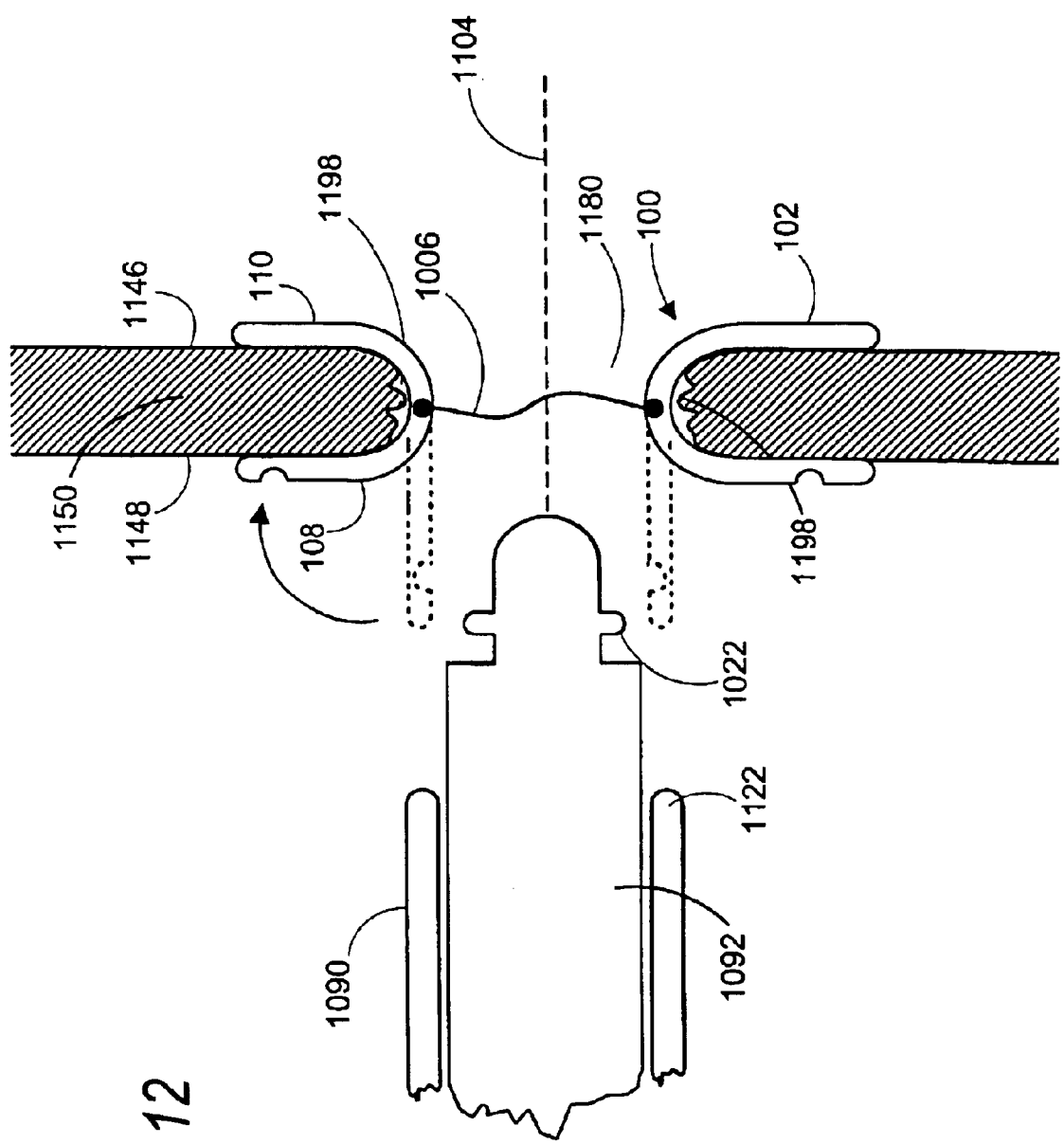
FIG. 12 is a cross-sectional view of the plug shown in FIG. 10 and 11 when the plug is fully deployed in the septal defect in accordance with this invention.

After catheter 1090 is partially reciprocated as shown in FIG. 11, catheter is further reciprocated as shown in FIG. 12. End 1122 is withdrawn past locking pins 1022 and retention device receptacles 1016. This allows fingers 108 to spring out radially away from central axis 1104 (from a position indicated by the dashed lines) and engage patient's cavity wall 1150 at surface 1148. As shown in FIG. 12, foldable plugging structure 1006 at least partially unfolds to span aperture 1180.

Figure 13:
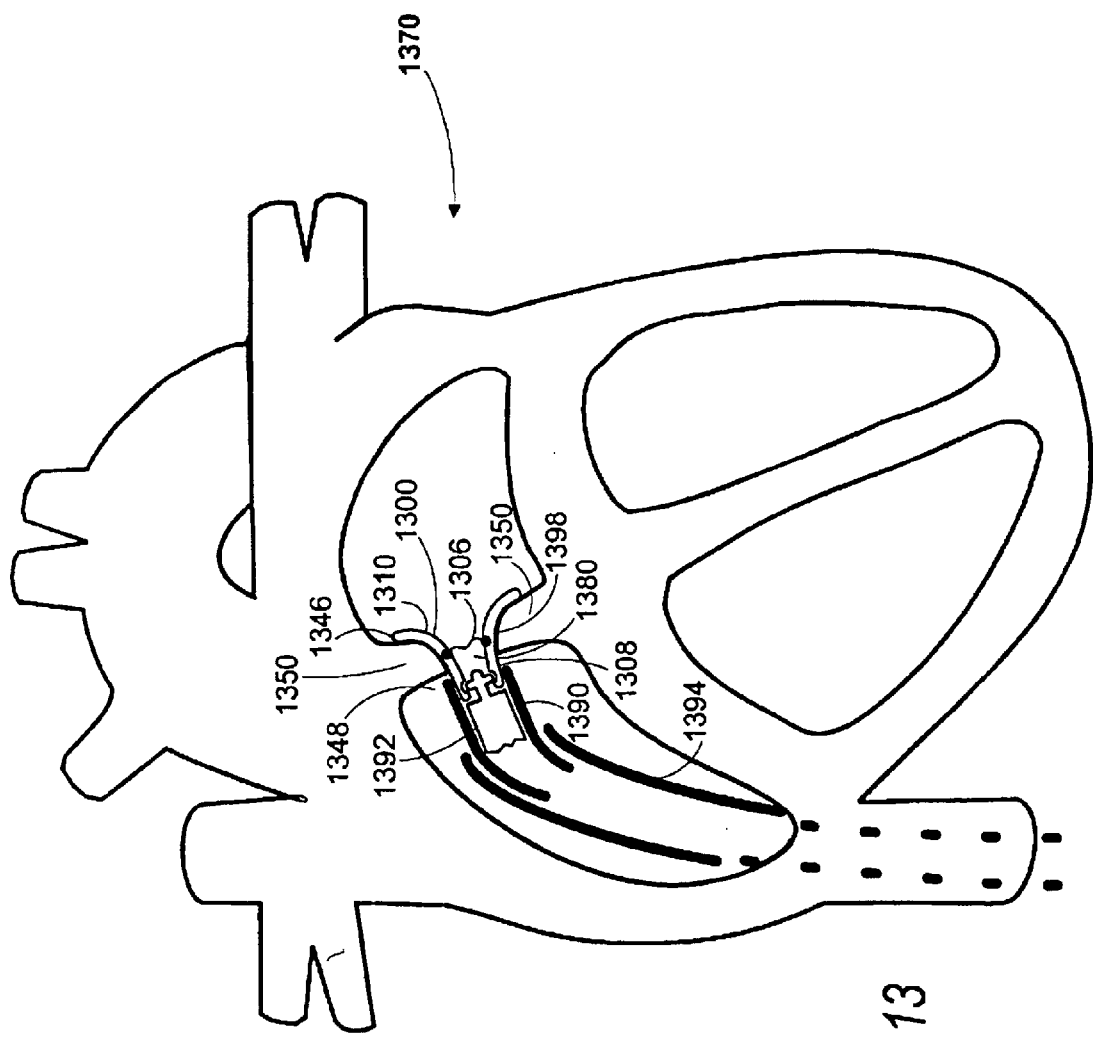
FIG. 13 is a cross-sectional view of a plug similar to the one shown in FIGS. 10–12 when the plug is fully deployed showing the delivery path of a delivery device in accordance with this invention.

FIG. 13 shows plug 1300 partially installed in aperture 1380 in wall 1350 of heart 1370. Plug 1300 of FIG. 13 corresponds roughly to plug 100 of FIG. 11. Delivery catheter 1390 and retention device 1392 are guided to wall 1350 by delivery guide 1394. At this stage of the installation, fingers 1310 are deployed and engaged with surface 1346 of wall 1350. Fingers 1308 remain in delivery catheter 1390. Plugging structure 1306 is positioned inside aperture 1380 and is ready to conform to perimeter 1398 of aperture 1380 when the remainder of plug 1300 is released from retention device 1392.

Figure 14:
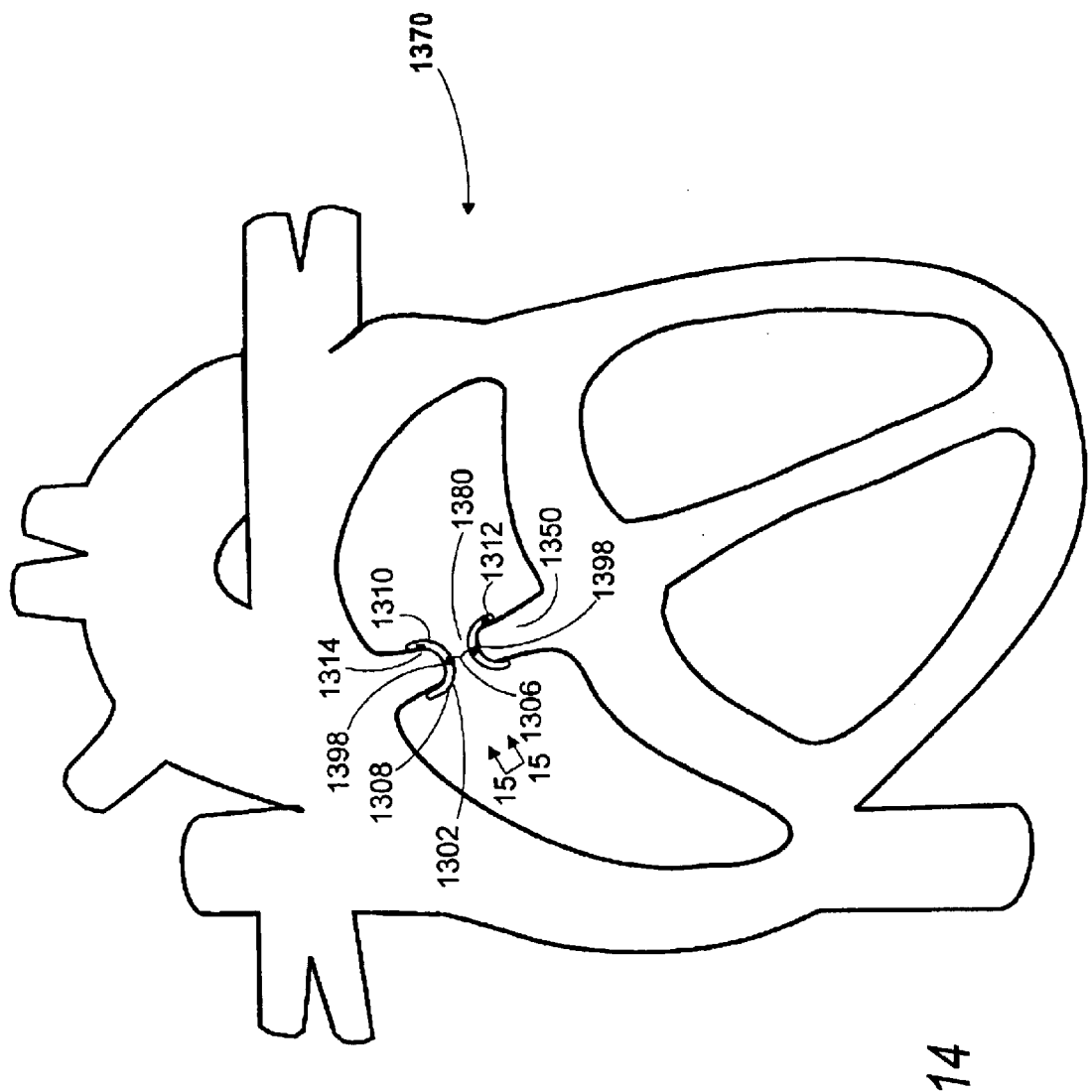
FIG. 14 is a cross-sectional view of the plug shown in FIG. 13 for plugging a septal defect when the plug is fully deployed and the delivery device has been retracted from the heart in accordance with this invention.
Figure 15:
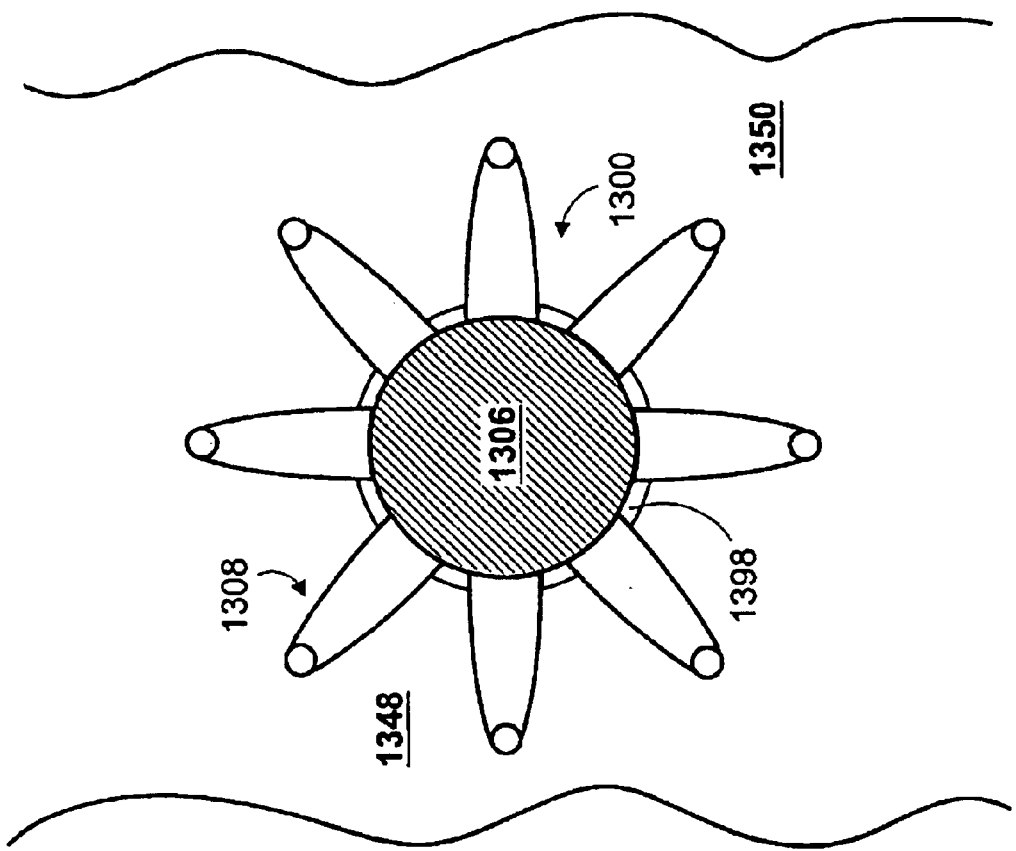
FIG. 15 is an elevational view of the plug shown in FIGS. 13 and 14 taken along line 15—15 of FIG. 14 in accordance with this invention.

FIG. 14 shows plug 1300 fully installed in aperture 1380 in heart 1370 so that plugging structure 1306 spans aperture 1380 and frame 1302 conforms to perimeter 1398. Fingers 1308 and 1310 are engaged with opposite sides of wall 1450 to secure plug 1300. Optional markers 1314 are provided on ends 1312 of fingers 1310. In one embodiment according to the invention, markers 1314 are radiopaque. FIG. 15 shows plug 1300 as installed in wall 1350 as viewed along direction 15—15 of FIG. 14. Fingers 1308 are pressing against surface 1348 of wall 1350. Plugging structure 1306 spans the aperture in wall 1350 and is substantially flush with perimeter 1398.

Figure 16:
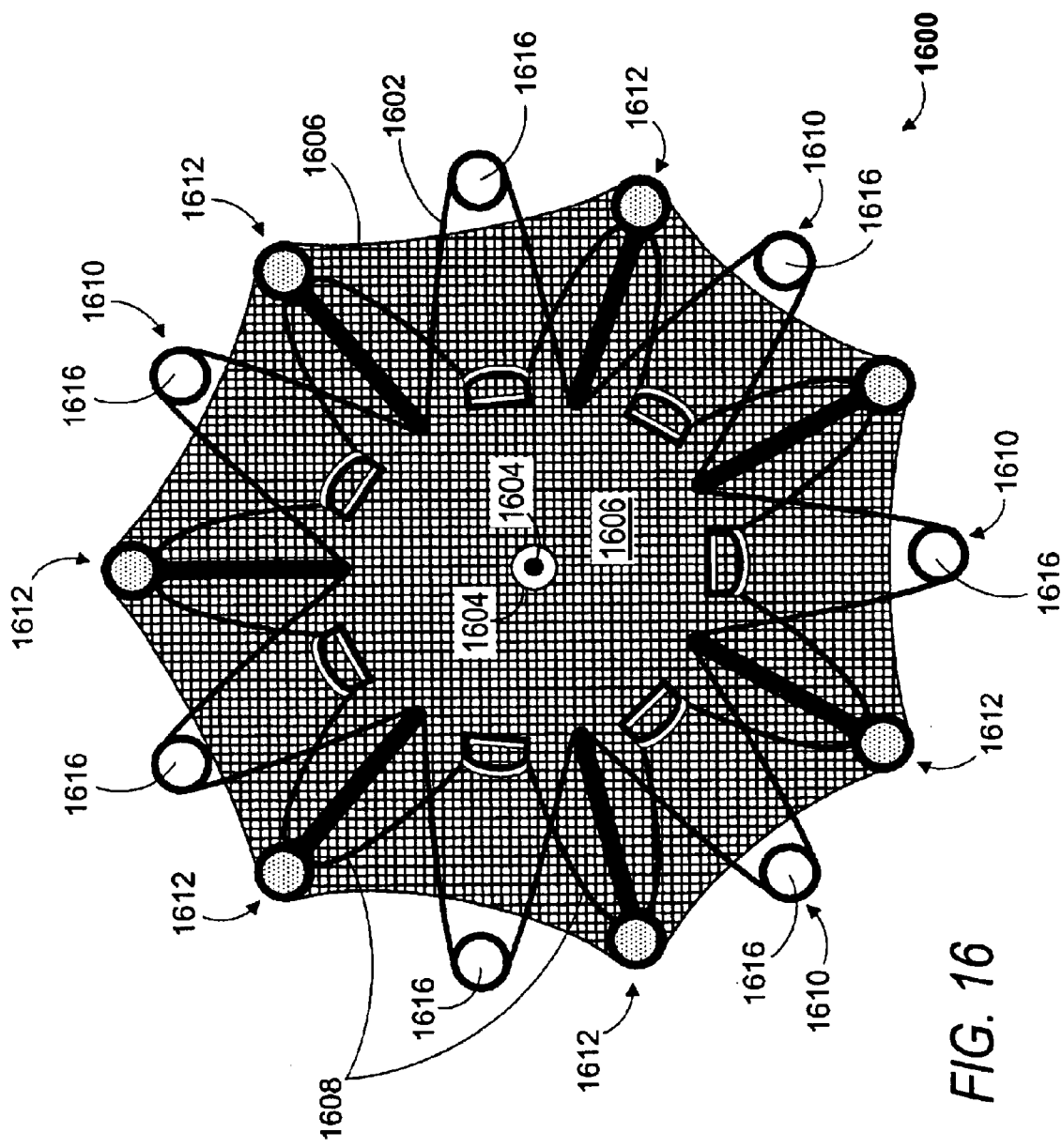
FIG. 16 is a plan view of yet another plug for plugging a septal defect in accordance with this invention.
Figure 17:
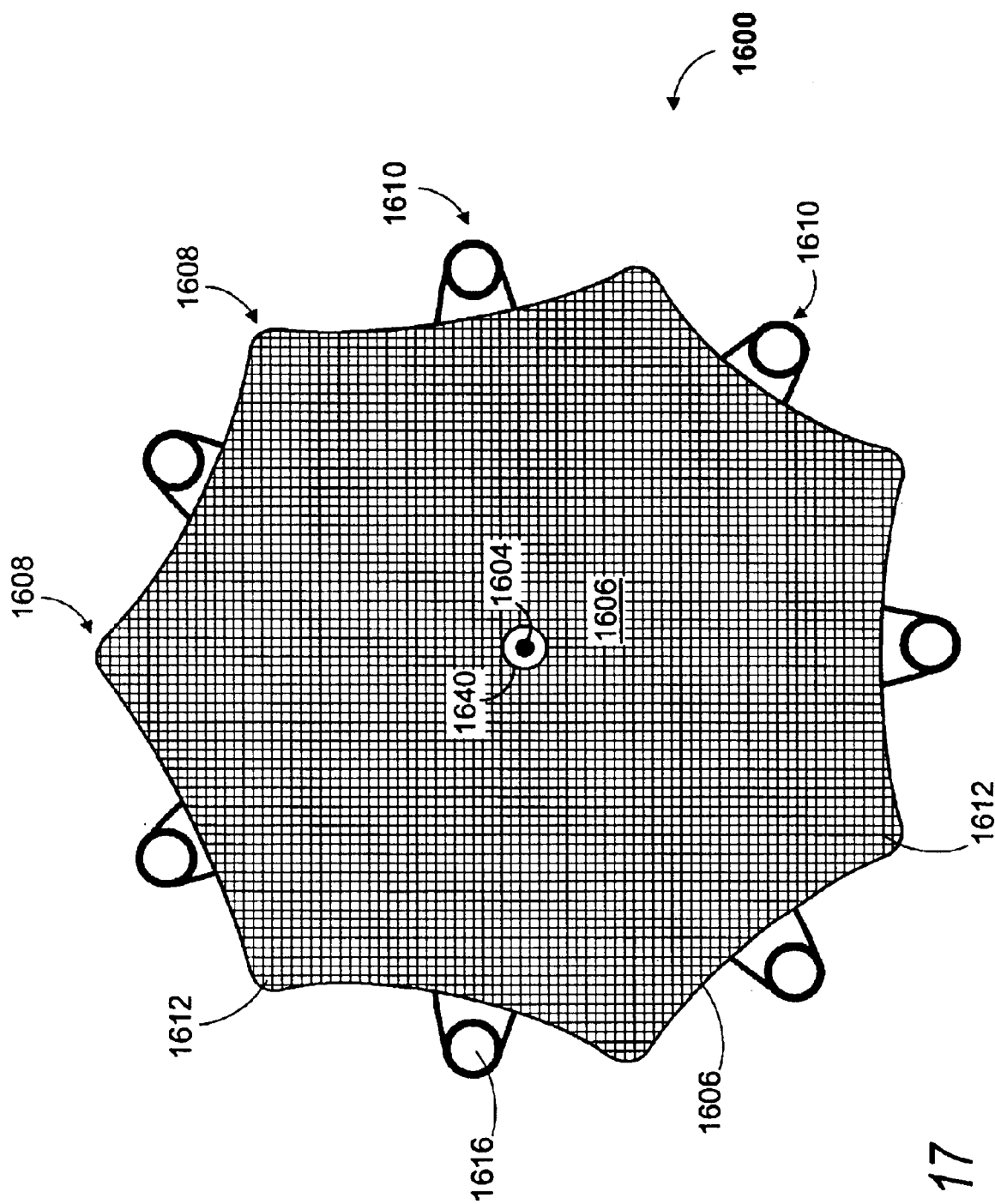
FIG. 17 is a plan view of the plug shown in FIG. 16 from the opposite side in accordance with this invention.

FIG. 16 shows another embodiment of a plug according to the invention. Plug 1600 includes frame 1602 which is structurally similar to frame 102 of FIG. 1. In this embodiment, however, plugging structure 1606 is supported by remote ends 1612 of fingers 1608. It will be appreciated that plugging structure could just as easily be mounted on fingers 1610. Optional marker rivets (not shown) can be placed in or near the apertures located at the of ends of fingers 1612. Optional marker rivets can also be used to attach plugging structure 1606 to frame 1602 and simultaneously provide a radiopaque marking device for locating and positioning plug 1600 using medical scanning instrumentation. Central axis 1604 passes through plugging structure 1606. Guide wire aperture 1640 allows a guide wire to be used to help control the position of plug 1600 during installation. FIG. 17 shows plug 1600 as viewed from the side opposite that shown in FIG. 16. As shown in FIG. 17, fingers 1610 and retention device receptacles 1616 can radially extend beyond plugging structure 1606.

Figure 18:
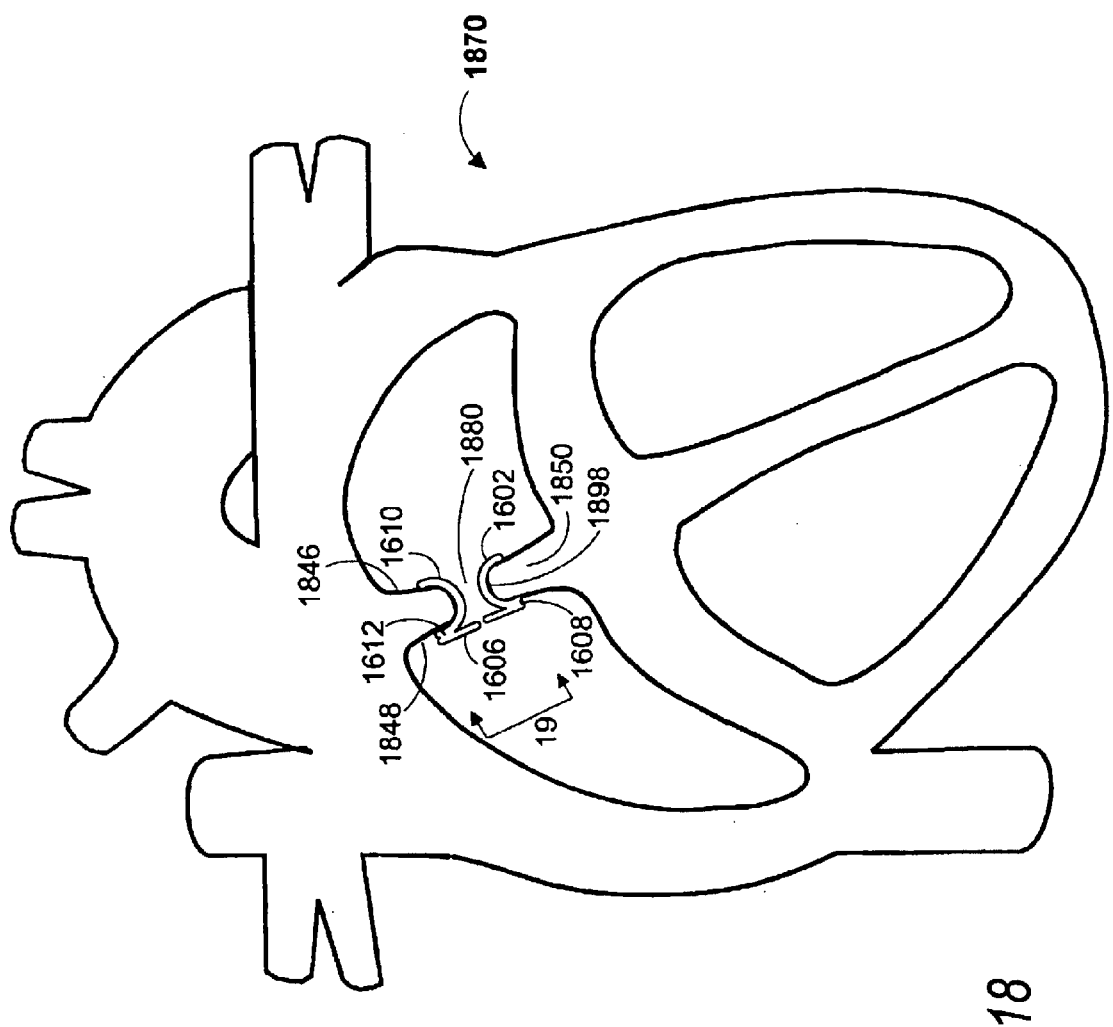
FIG. 18 is a cross-sectional view of the plug shown in FIGS. 16 and 17 when the plug is fully deployed in the septal defect in accordance with this invention.

FIG. 18 shows plug 1600 fully installed in aperture 1880 of wall 1850 of patient's heart 1870. Plugging structure 1606 is attached to remote ends 1612 of fingers 1608 and is drawn against surface 1848 by fingers 1612 as fingers 1608 press against side 1848. When installed, plugging structure 1606 has a greater diameter than cavity wall aperture 1880 and thus extends beyond perimeter 1898 of aperture 1880 in order to occlude aperture 1880. Fingers 1610 engage side 1846 of wall 1850 and hold plug 1600 in position.

Figure 19:
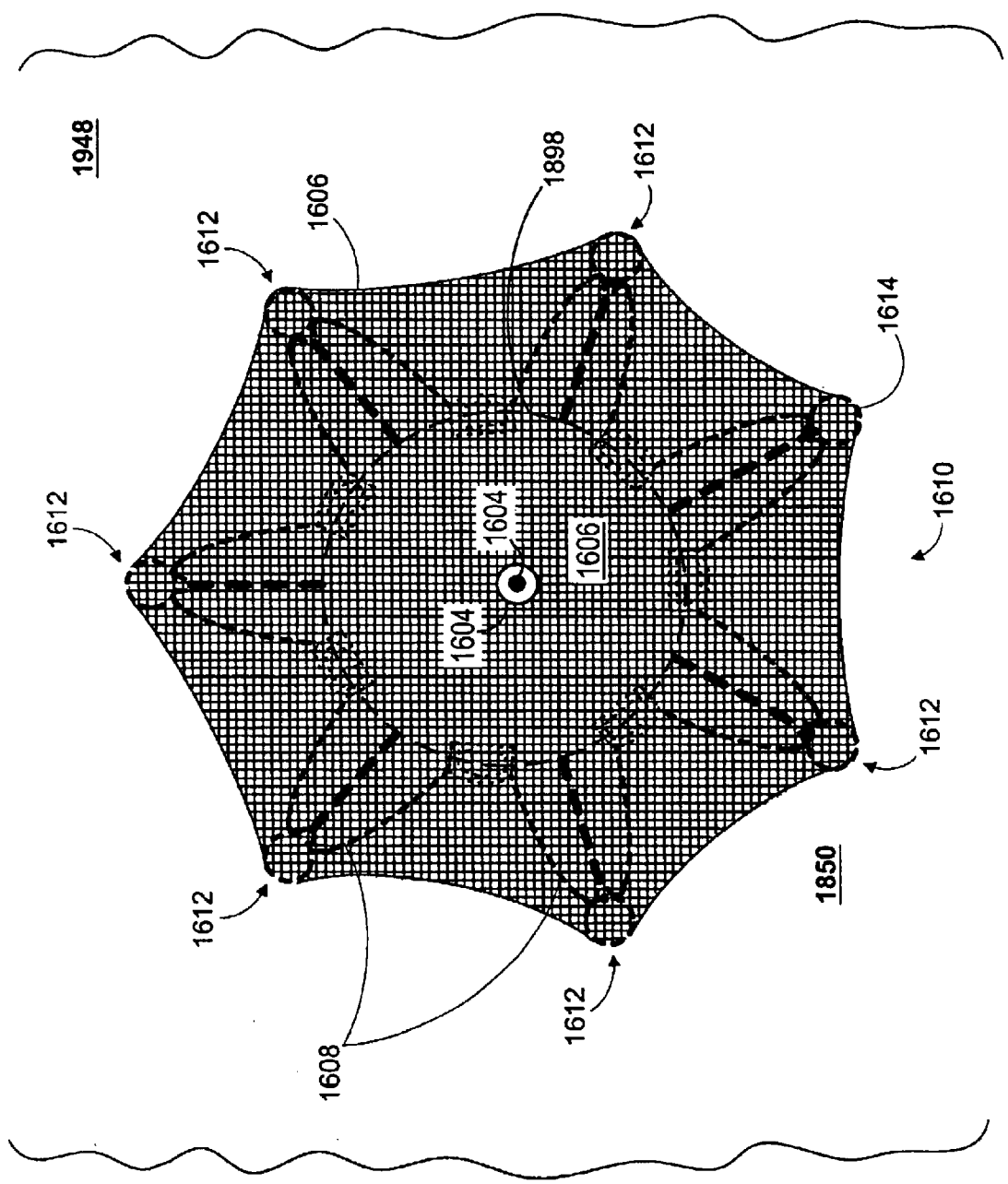
FIG. 19 is a plan view of the plug shown in FIGS. 16–18 taken from line 19—19 of FIG. 18 in accordance-with this invention.

FIG. 19 shows plug 1600 as viewed from line 19—19 of FIG. 18. Fingers 1610 of frame 1602 are not shown because from this perspective they are behind wall 1850. Perimeter 1898 of aperture 1880 is shown as a broken line because it is behind plugging structure 1606. Plugging structure 1606 can be supported by rivets 1614, which are located at ends 1612.

Figure 20:
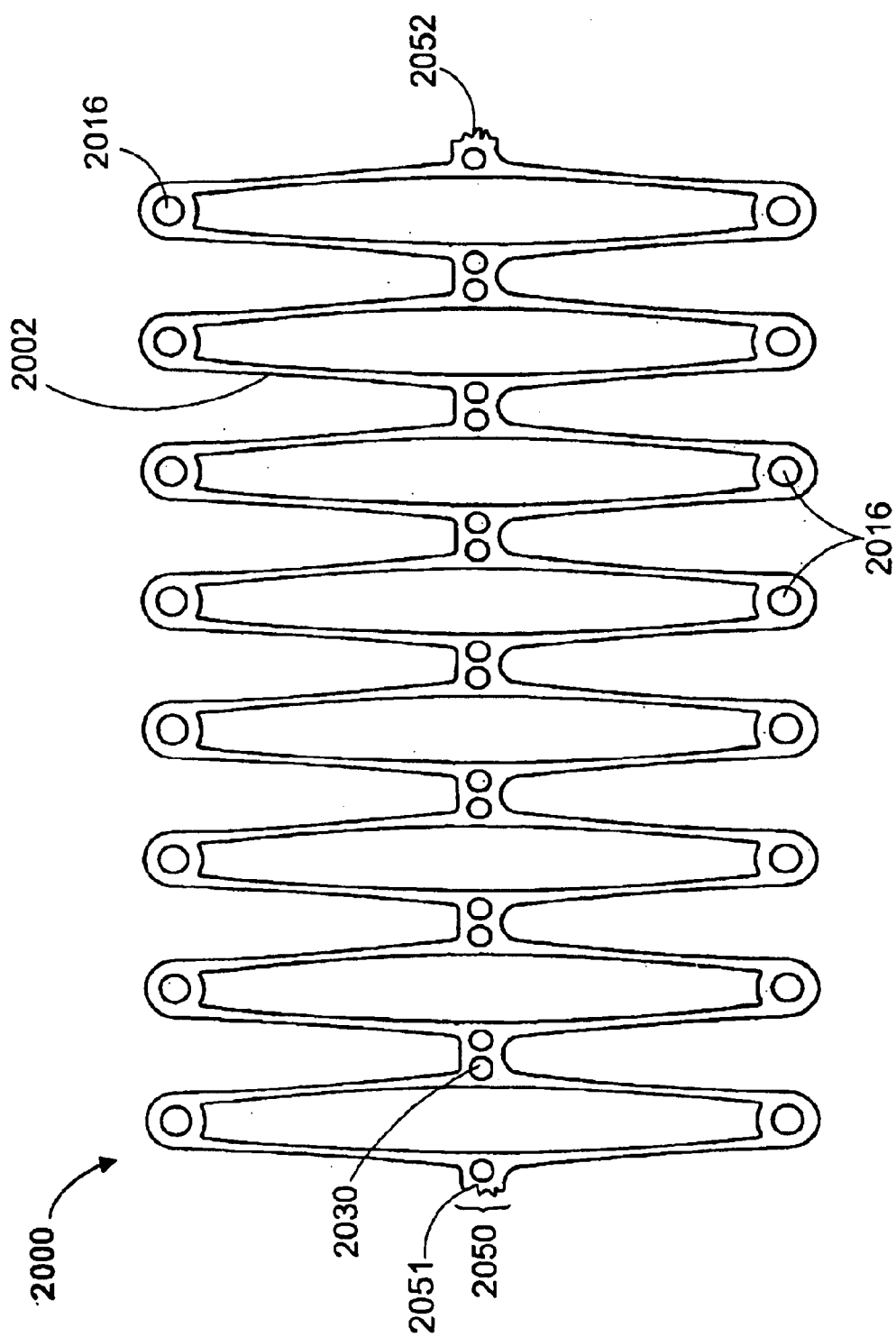
FIG. 20 is a partial elevational view of an unrolled frame for an illustrative plug in accordance with this invention.

According to one embodiment, a plug has a medial portion that defines a central passage with a central axis. To allow the medial portion to expand radially, any cross-section of that portion (and preferably the entire frame) taken perpendicularly to the central axis is substantially discontinuous. FIG. 20 shows frame 2002 in an "unfurled" state. Portions 2051 and 2052 of medial section 2050 would normally be connected so that medial section 2050 forms a perforated tube surrounding the plug's central axis. Plug 2000 can include retention device receptacles 2016 on, for example, remote ends of the fingers. Frame 2002 can also include support structures 2030 for supporting a plugging structure (not shown).

Figure 21:
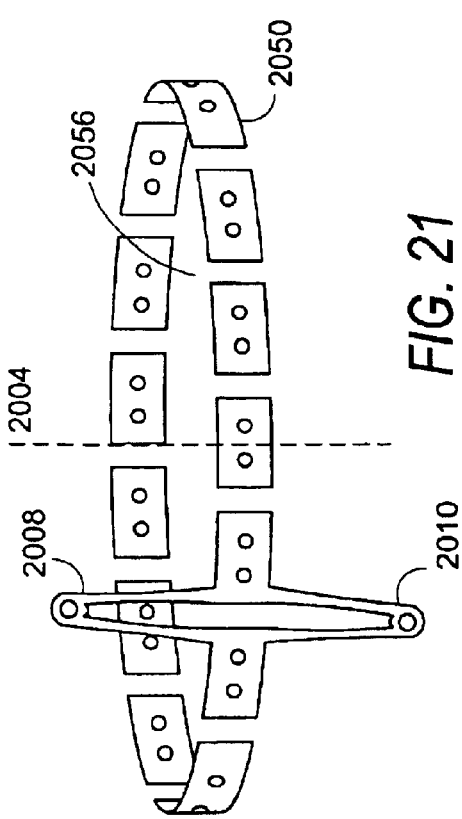
FIG. 21 is a perspective view of the of the frame shown in FIG. 21 with ends attached (showing only a single finger at each axial end of the frame) in accordance with this invention.

Medial section 2050, when in its operable shape, forms a perforated tubular portion. FIG. 21 is a perspective view of frame 2002 in its operable tubular shape, including particularly medial section 2050 and fingers 2008 and 2010 (remainder of fingers not shown for the sake of simplicity). Perforated tubular portion 2050 defines longitudinal passage 2056 along central axis 2004.

Figure 22:
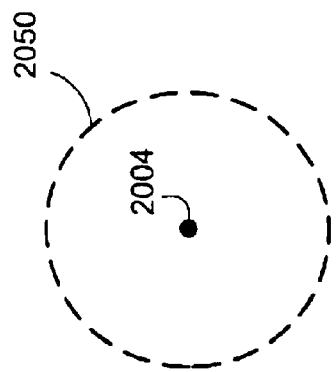
FIG. 22 is a cross-sectional view of the frame shown in FIGS. 20 and 21 with ends attached in accordance with this invention.

FIG. 22 shows a cross-sectional view of perforated tubular portion 2050 taken along a plane that is perpendicular to central axis 2004. The broken line corresponding to portion 2050 indicates that the cross section is discontinuous.

Figure 23:
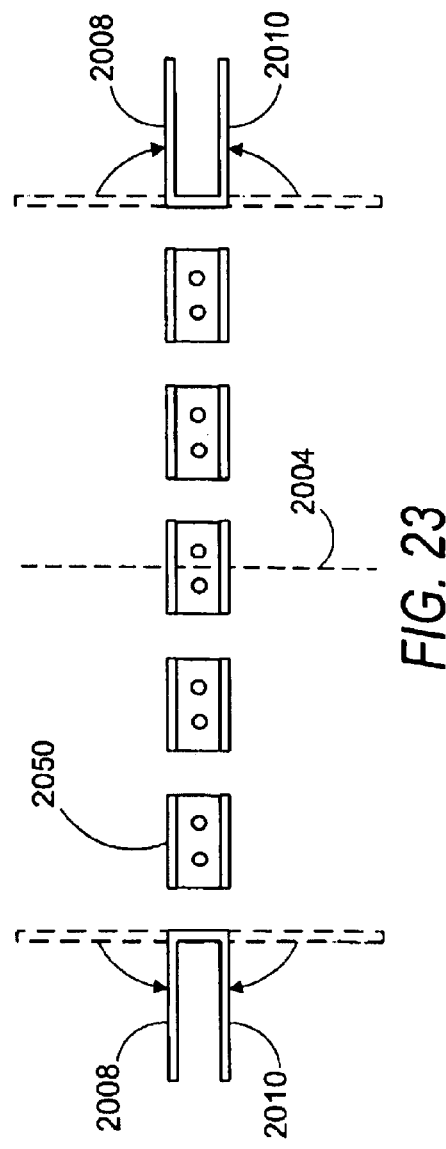
FIG. 23 is an elevational view of the frame shown in FIG. 22 in accordance with this invention.

FIG. 23 shows a side view of tubular portion 2050 and selected fingers 2008 and 2010 in two different positions. As shown, fingers 2008 and 2010 are attached to the axial ends of tubular portion 2550 and are bent away from central axis 2004 into a splayed position. These fingers can be heat treated before the plug is installed to cause them to relax in this splayed position. Fingers 2008 and 2010 can also be positioned so that they point in a direction that is substantially parallel to central axis 2004 (as shown by dashed lines, which corresponds to the view of FIG. 22) for installation of the plug. This position can be achieved, for example, by inserting the plug into a delivery device.

Figure 24:
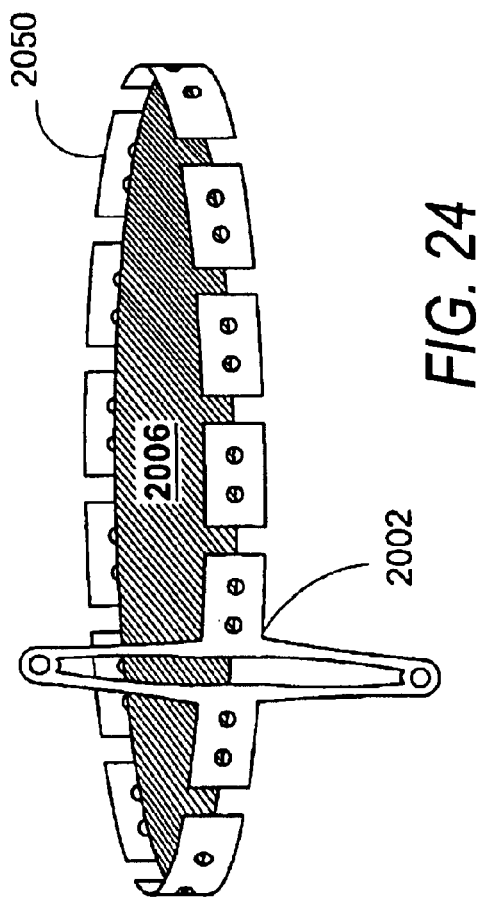
FIG. 24 is a perspective view of the frame shown in FIG. 21 with an attached plugging structure to form a plug in accordance with this invention.
Figure 25:
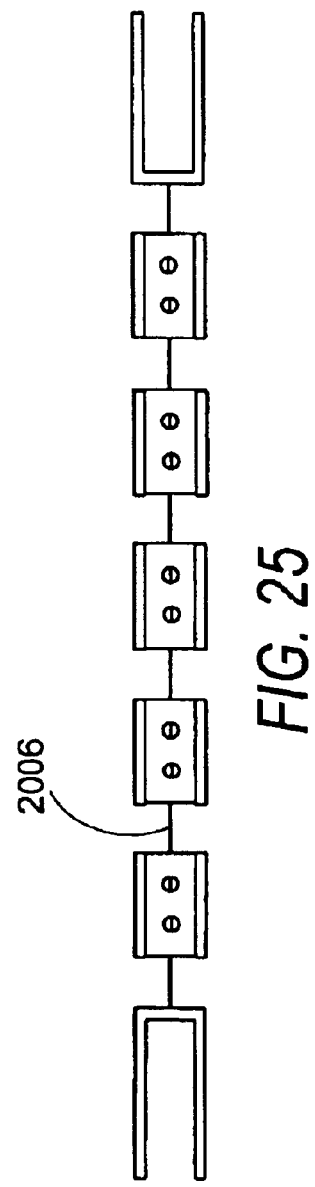
FIG. 25 is an elevational view of the plug shown in FIG. 24 (showing a number of forward facing fingers) after the fingers have been bent into the wall-engaging position in accordance with this invention.
Figure 26:
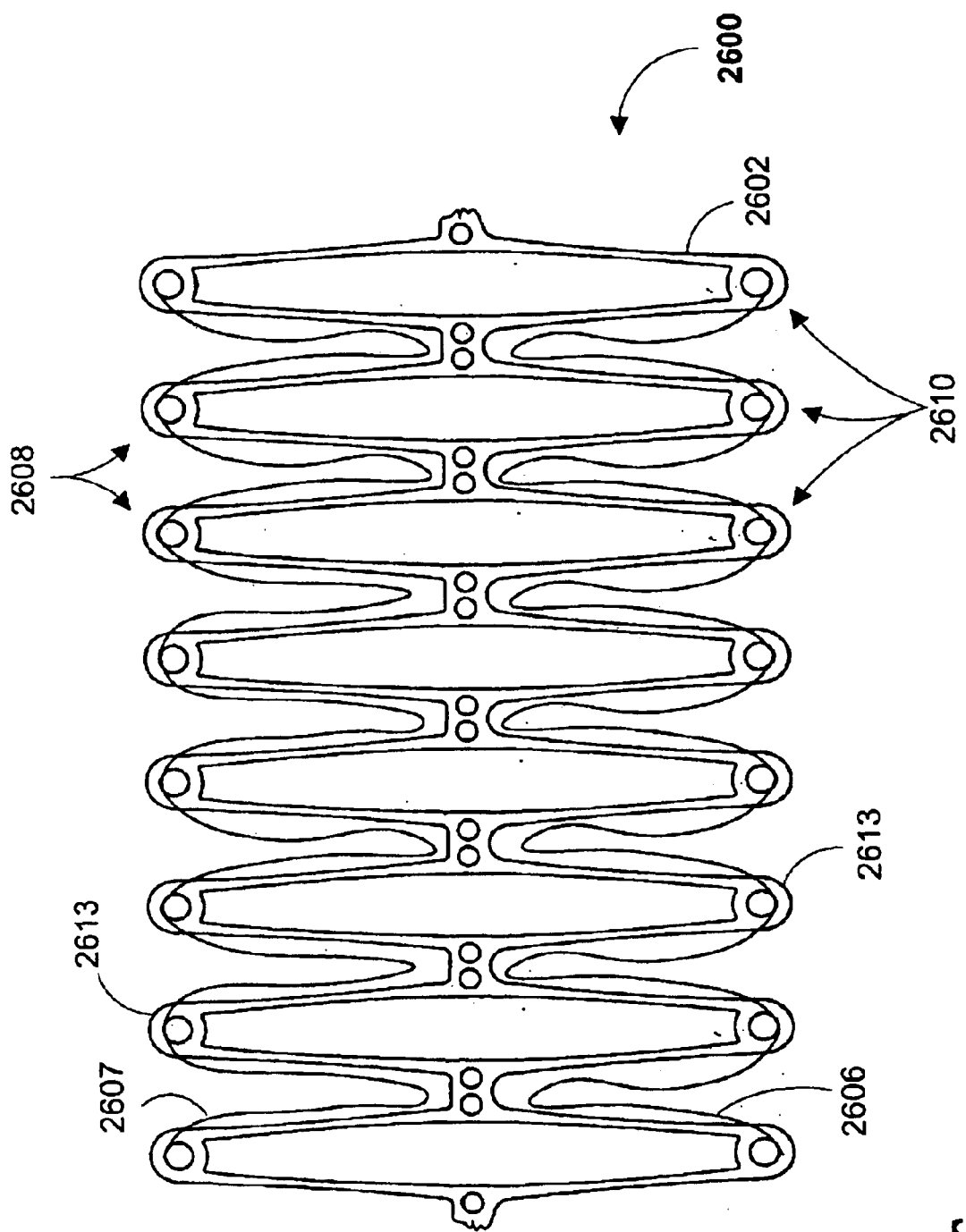
FIG. 26 is a partial elevational view of an unrolled frame with a plugging structure in accordance with this invention.

FIGS. 24 and 25 are similar to FIGS. 21 and 23, respectively, but now include plugging structure 2006 mounted to frame 2002. Alternatively, a plugging structure can be supported by support structures 2013 of fingers 2008 and/or 2010. Alternatively, plug 2000 can include two plugging structures, each of which can be supported by support structures located at opposite axial ends of plug 2000. For example, plug 2600, which includes frame 2602, is shown in FIG. 216 in an unfurled position for illustrative purposes. Frame 2602 includes first plugging structure 2606, which is mounted on support structures 2613 of fingers 2610 and second plugging structure 2607, which is mounted on support structures 2613 of fingers 2608. Support structures 2613 can also be used to mount markers or engage a retention device.

Figure 27:
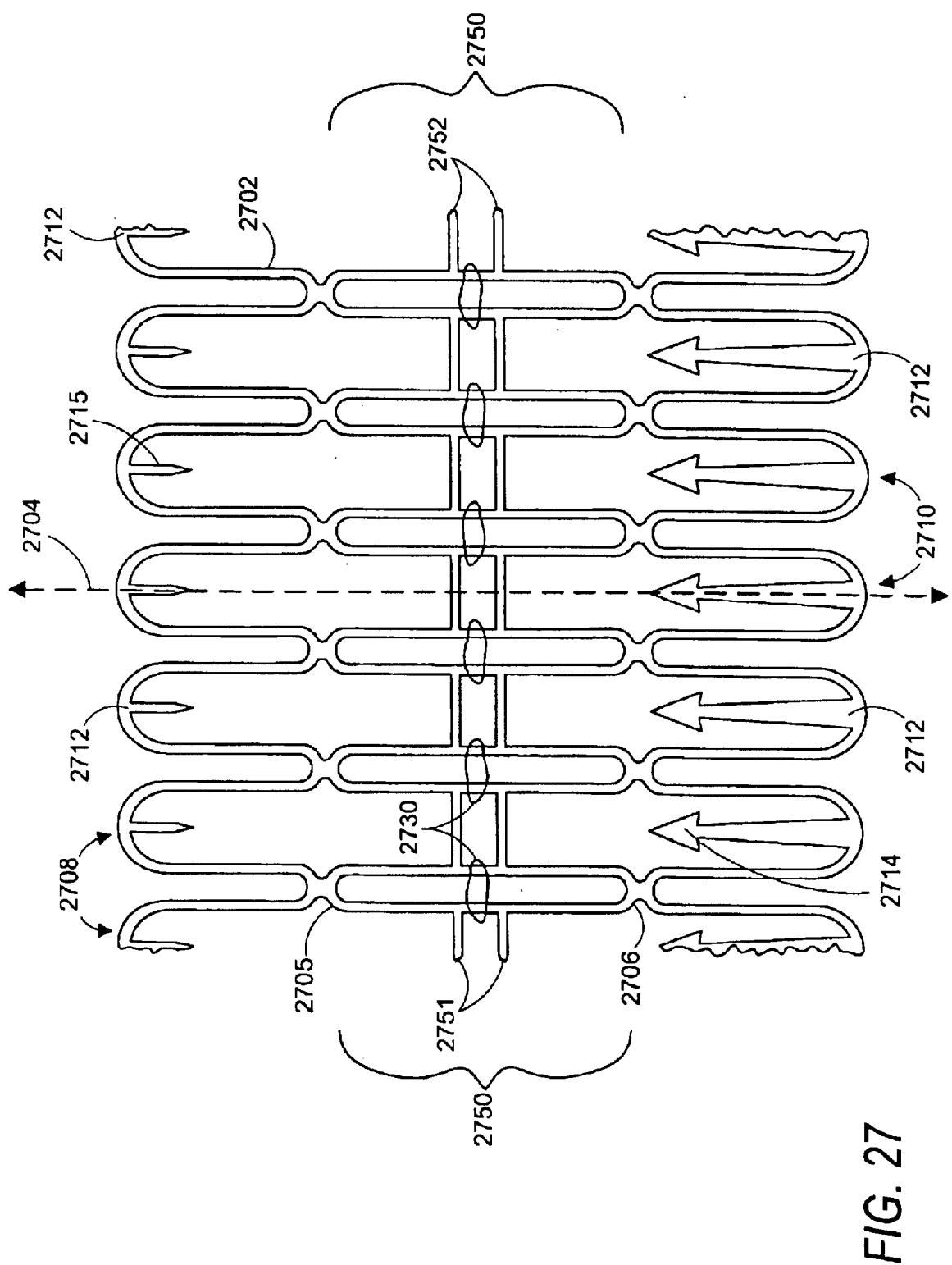
FIG. 27 is an elevational view of another unrolled frame for a plug in accordance with this invention.

In another embodiment according to this invention, a frame having a perforated tubular portion can be formed from a plastically deformable material and can be installed using a balloon. FIG. 27, for example, shows frame 2702 in an unfurled state similar to the configuration of frame 2002 in FIGS. 20 and 26. In use, end portion 2751 and 2752 are joined to form a tubular structure surrounding central axis 2704. (Frame 2702 can be formed from a tube, thereby eliminating the need to join portions 2751 and 2752.)

When portions 2751 and 2752 are joined, medial section 2750 becomes a perforated tubular portion corresponding to perforated tubular portion 2050 shown in FIG. 22. Although the perforated tubular portion shown in FIG. 27 is axially longer than the perforated tubular portion shown in FIGS. 21 and 22, it will be appreciated that the length of the tubular portion can be matched to the thickness of the wall being plugged.

As shown in FIG. 27, fingers 2708 and fingers 2710 extend from opposite axial ends 2705 and 2706 of portion 2750, respectively. A plugging structure (not shown) can be attached, for example, to support structures 2730 to occlude the longitudinal passage during use. Piercing points 2715 and barbs 2714 are for engaging opposite sides of a wall for securing frame 2702 thereto.

Figure 28:
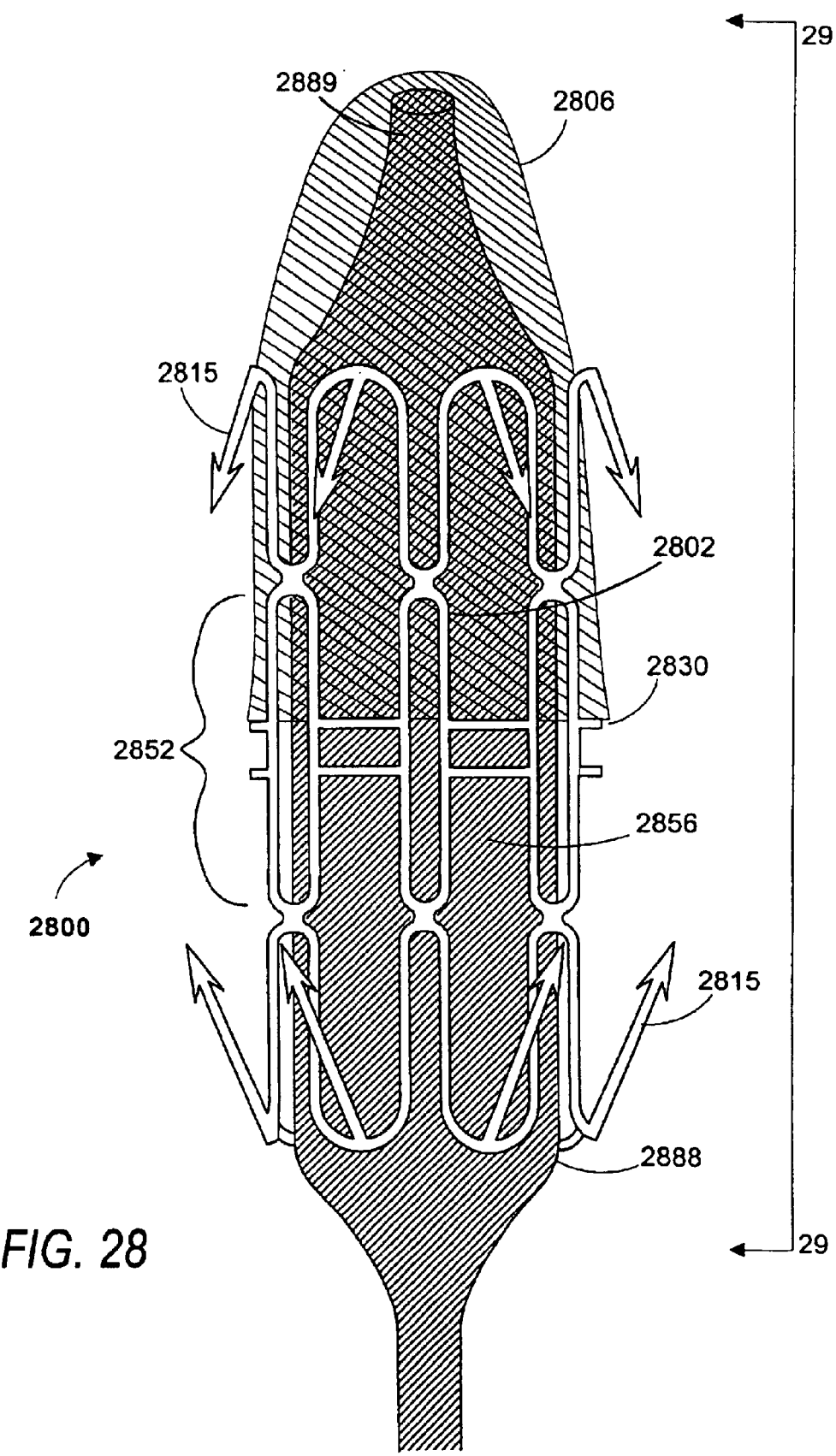
FIG. 28 is an elevational view of another plug mounted on a delivery balloon in accordance with this invention.

FIG. 28 shows plug 2800, which includes frame 2802 with delivery balloon 2888 inserted in longitudinal passage 2856. Delivery balloon 2888 is inflated enough to engage frame 2802 and allow delivery of plug 2800 to a repair site inside a patient. Folded or elastic plugging structure 2806 is deflected around tip 2889 of balloon 2888. Plugging structure 2806 is attached to frame 2802 at support structure 2830. Plug 2800 can have barbs 2815, for example, for engaging a patient's body tissue.

Figure 29:
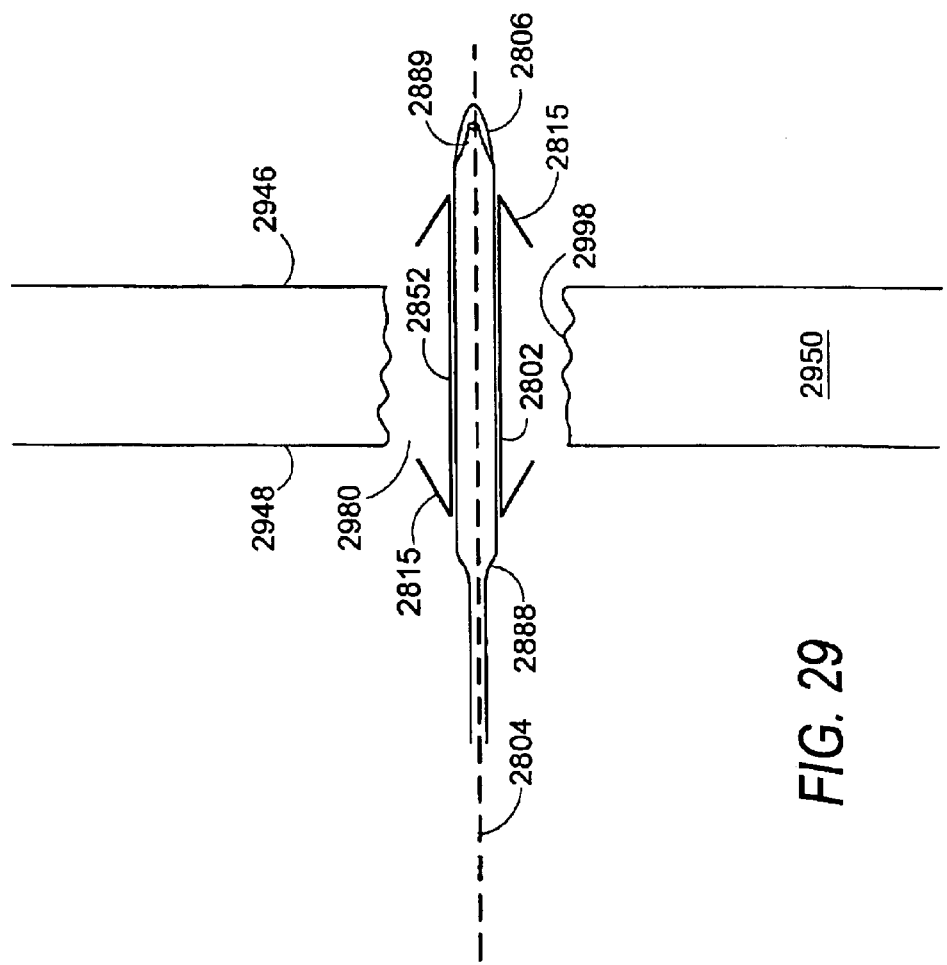
FIG. 29 is a cross-sectional view taken of the plug shown in FIG. 28 in position for deployment in a defect in accordance with this invention.

FIG. 29 shows a cross-sectional view of plug 2800 being positioned in aperture 2980 in cavity wall 2950. During installation of plug 2800, balloon 2888 engages the inside of frame 2802. Plugging structure 2806 is deflected around balloon tip 2889. Next, plug 2800 is inserted with balloon 2888 into aperture 2980. Balloon 2888 is then inflated, causing frame 2802 to expand radially and to contract along its central axis 2804, thereby forcing barbs 2815 to pierce opposite sides 2946 and 2948 of wall 2950. This also causes perforated tubular portion 2852 to conform to perimeter 2898. If plugging structure 2806 is secured to perforated tubular portion 2852, it too is stretched or unfolded across aperture 2980.

Figure 30:
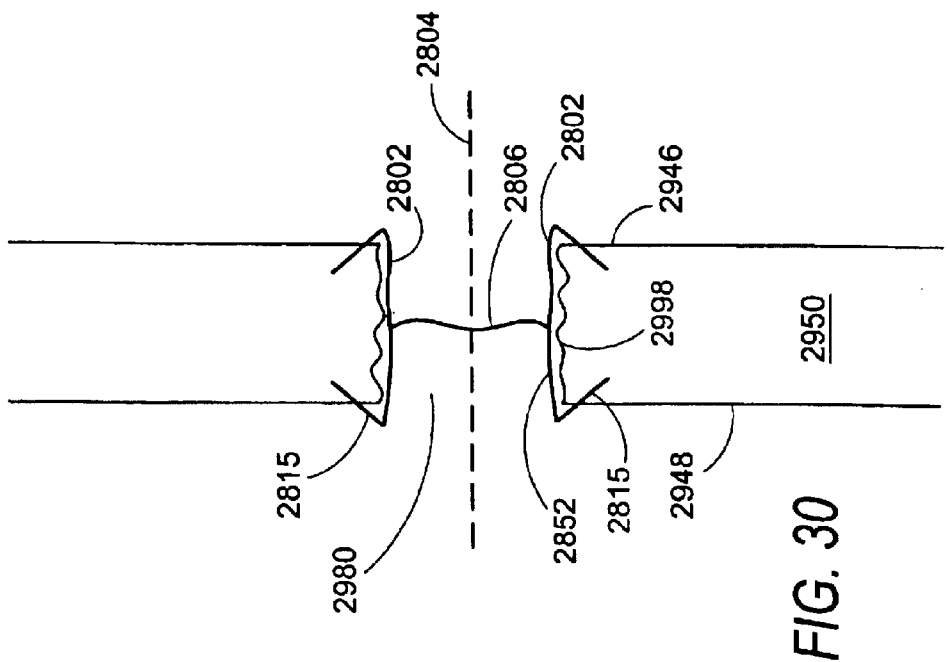
FIG. 30 is a cross-sectional view of the plug shown in FIGS. 28 and 29 when the plug is deployed in the defect in accordance with this invention.

FIG. 30 shows plug 2800 installed in aperture 2980 after frame 2802 is deformed by the expansion of balloon 2888. At this stage, balloon 2888 has been removed from perforated tubular portion 2852. The perforations (i.e., the holes) in portion 2852 allow the axial length of perforated tubular portion 2852 to decrease as its radius increases.

Figure 31:
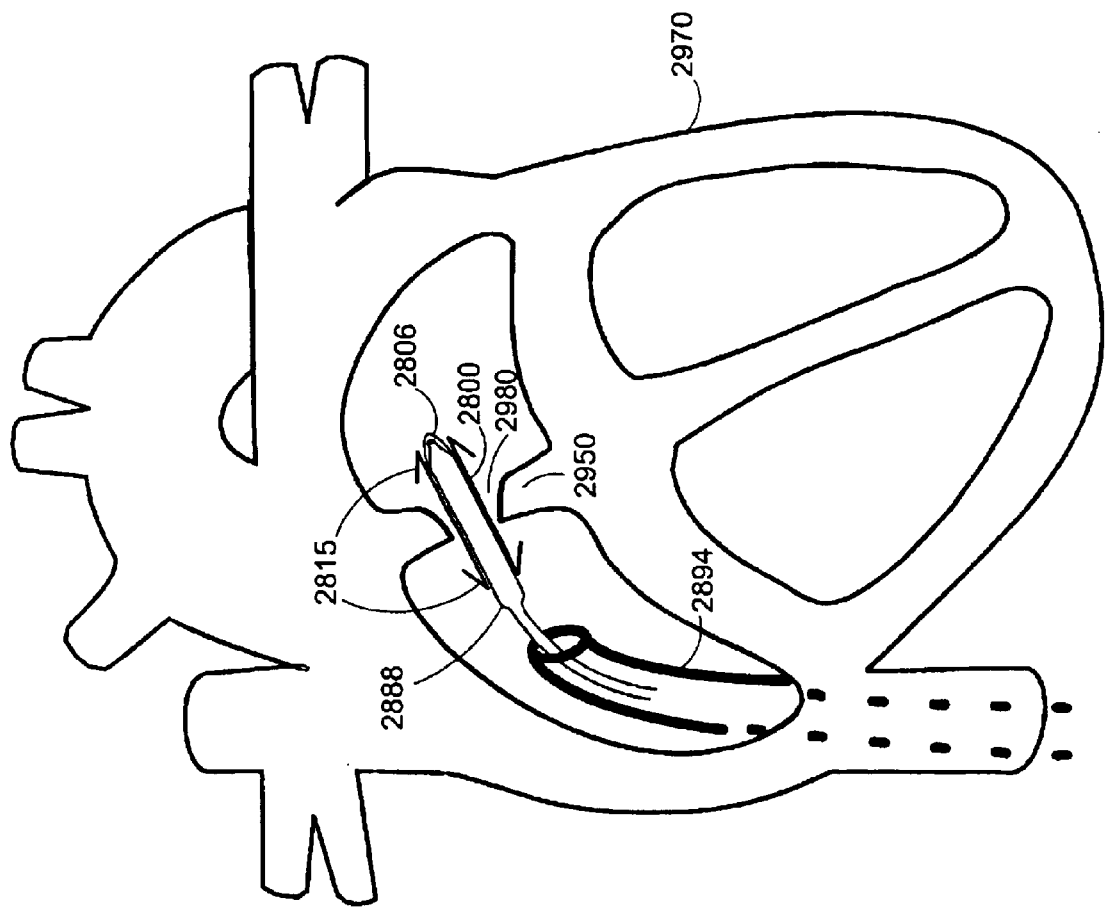
FIG. 31 is a cross-sectional view of the plug shown in FIGS. 28–30 in position for deployment showing the delivery path of a delivery device in accordance with this invention.

FIG. 31 shows plug 2800 being delivered to aperture 2980 in heart 2970. Plug 2800 is supported by partially inflated balloon 2888 and guided through a patient's body tissue and/or tubing via delivery guide 2894 until it is positioned with barbs 2815 on opposite sides of wall 2950.

Figure 32:
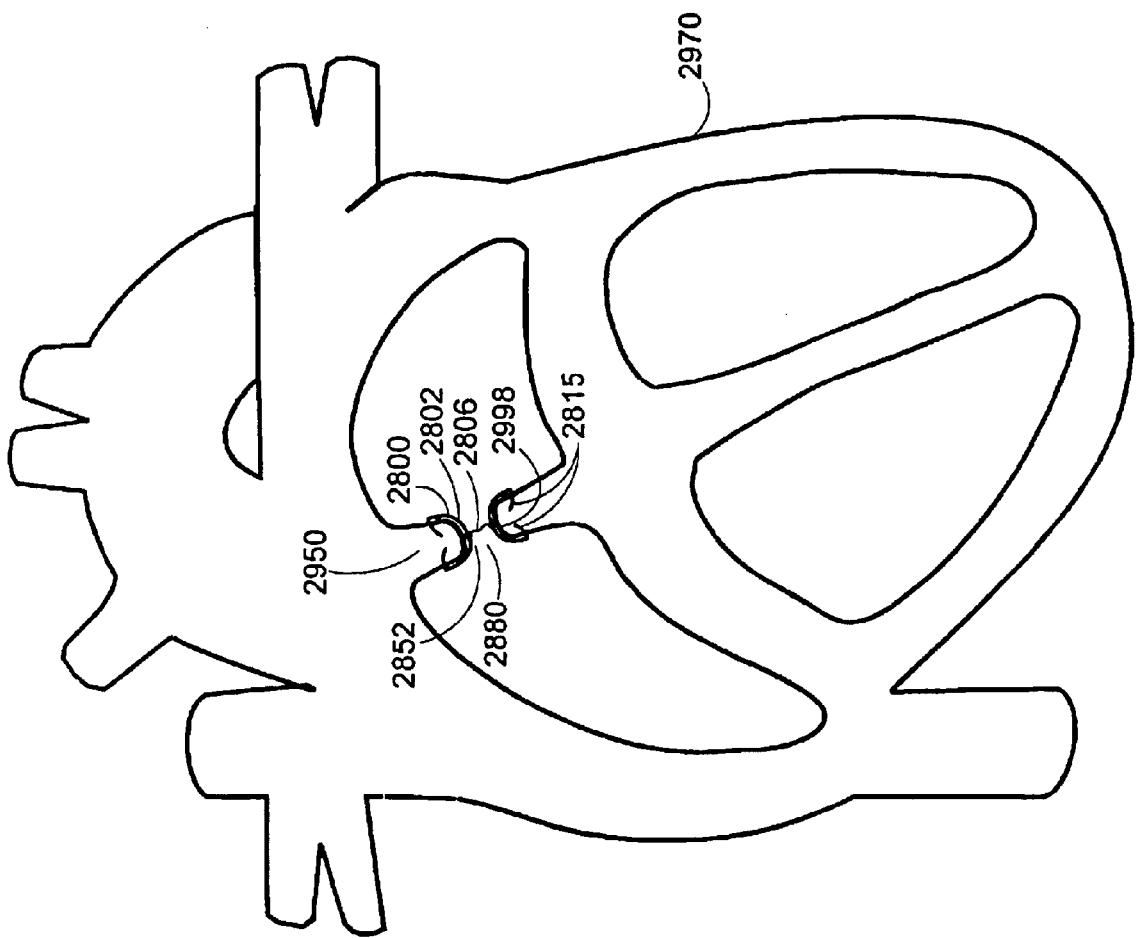
FIG. 32 is a cross-sectional view of yet another plug for plugging a septal defect when the plug is fully deployed in the septal defect in accordance with this invention.

After delivery of plug 2800 to aperture 2980, plug 2800 can be fully installed by further expanding balloon 2888, thereby causing frame 2802 to deform and secure itself as shown in FIG. 32. After plug 2800 is secured, balloon 2888 is deflated and removed. When installed, tubular portion 2852 conforms to perimeter 2998 and plugging structure 2806 spans and occludes blood flow through the aperture.

Figure 33:
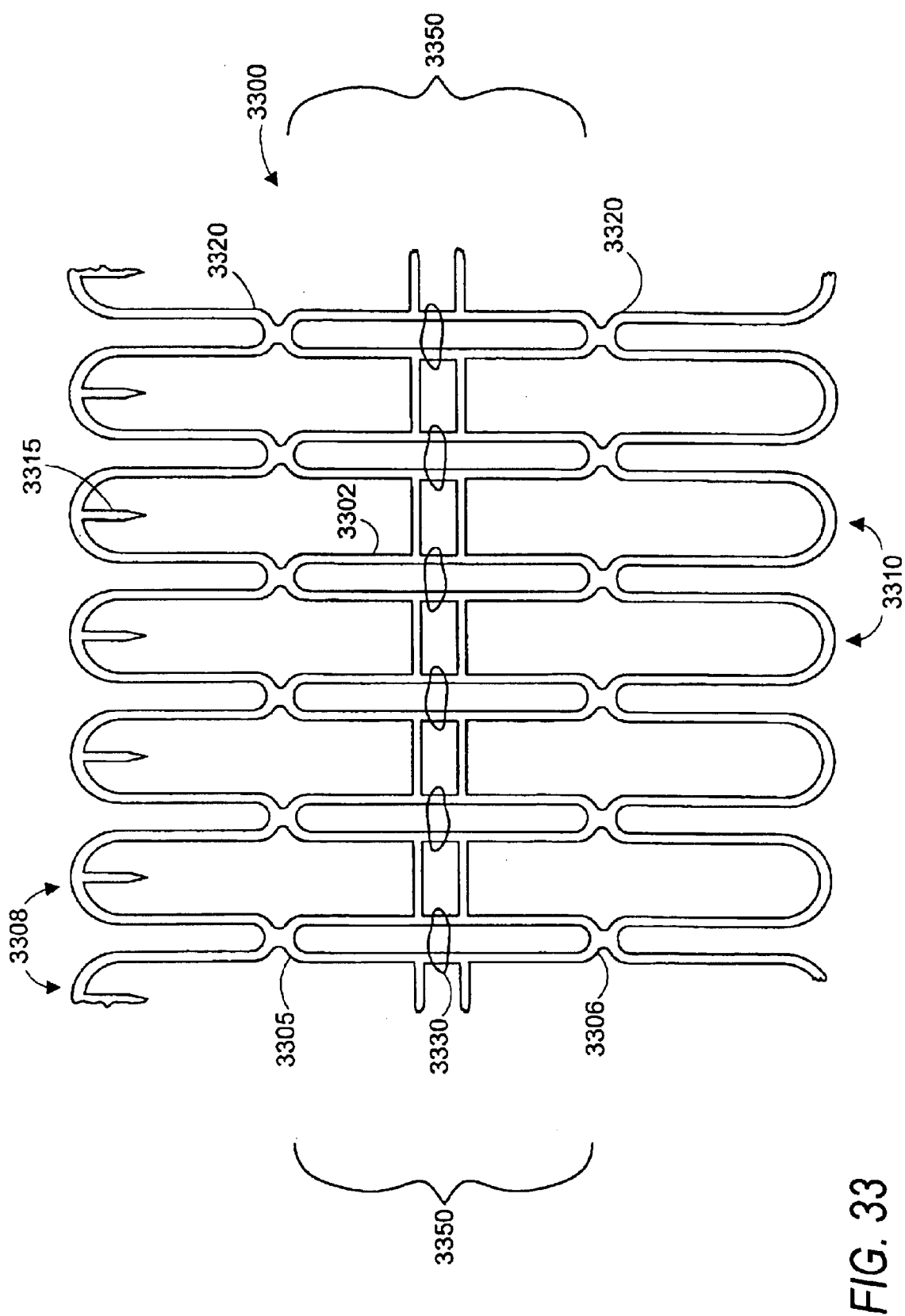
FIG. 33 is a partial elevational view of an unrolled frame for an occlusion device (i.e., a plug) in accordance with this invention.

In another embodiment of the invention, a plug is provided for occluding a lumen of a patient's body tubing. FIG. 33 shows occlusion plug 3300, which includes frame 3302. Plug 3300 is similar to aperture plug 2700 (shown in FIG. 27), but has barbs (or points) that extend from fingers 3308 on only one axial end 3305 of medial section 3350. It will be appreciated that points 3315 are not always necessary, but may be included in plugs where positive anchoring is desired. Frame 3302 is shown in FIG. 33 in an "unfurled" state, but as in the embodiments discussed above, would be joined to form a perforated tubular portion. Support structures 3330 can also be provided for securing a plugging structure (not shown).

Figure 34:
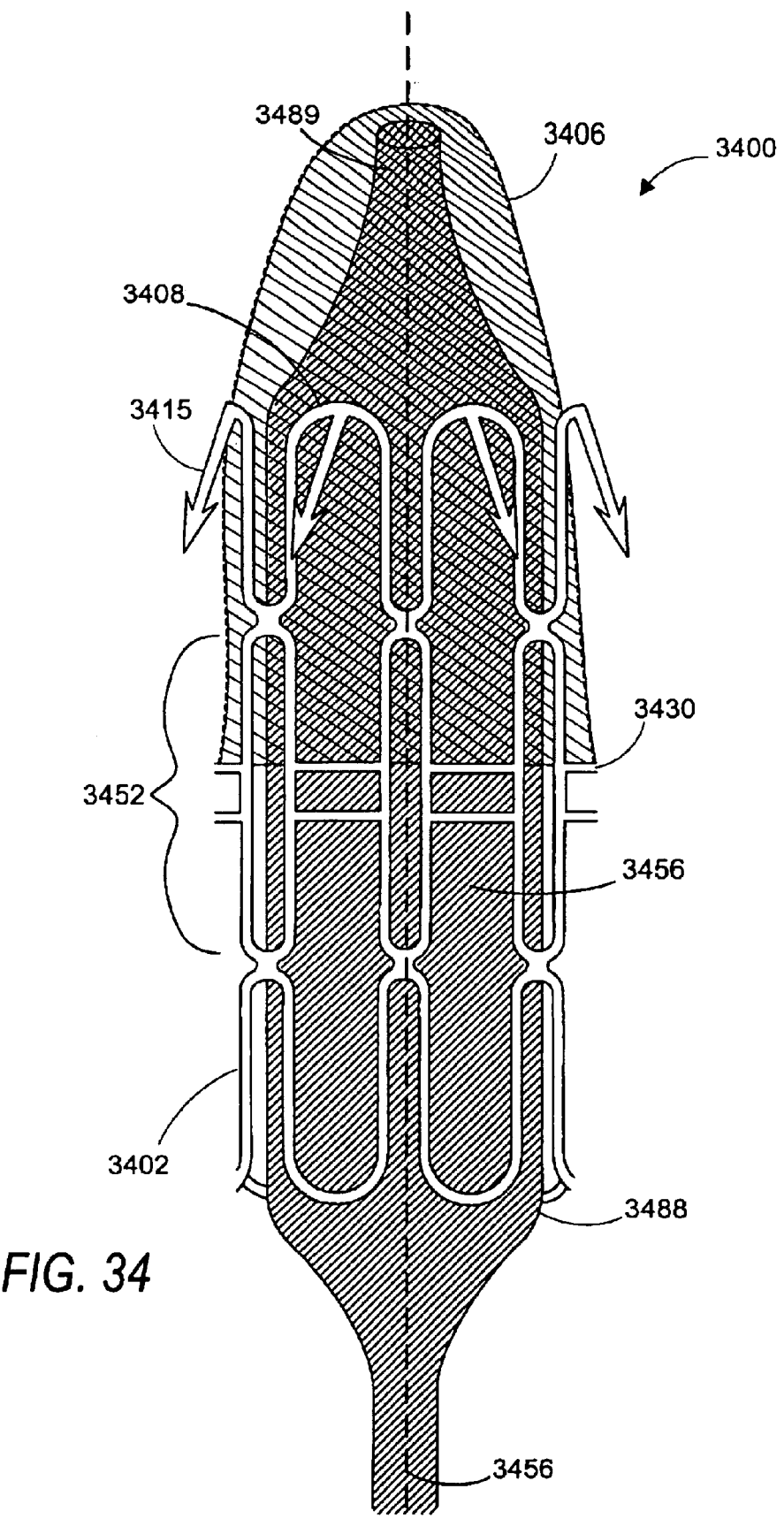
FIG. 34 is an elevational view of another occlusion device with barbs mounted on a delivery balloon in accordance with this invention.

FIG. 34 shows occlusion plug 3400 mounted on partially inflated balloon 3488. Balloon 3488 occupies longitudinal passage 3456 along central axis 3456. Plugging structure 3406 is attached to frame 3402 at support structures 3430 in medial section 3452 and is deflected around tip 3489 of balloon 3488. Piercing points 3415, which can be barbed, extend away from central axis 3456 and are destined to be embedded in the interior wall of a patient's body tubing.

Figure 35:
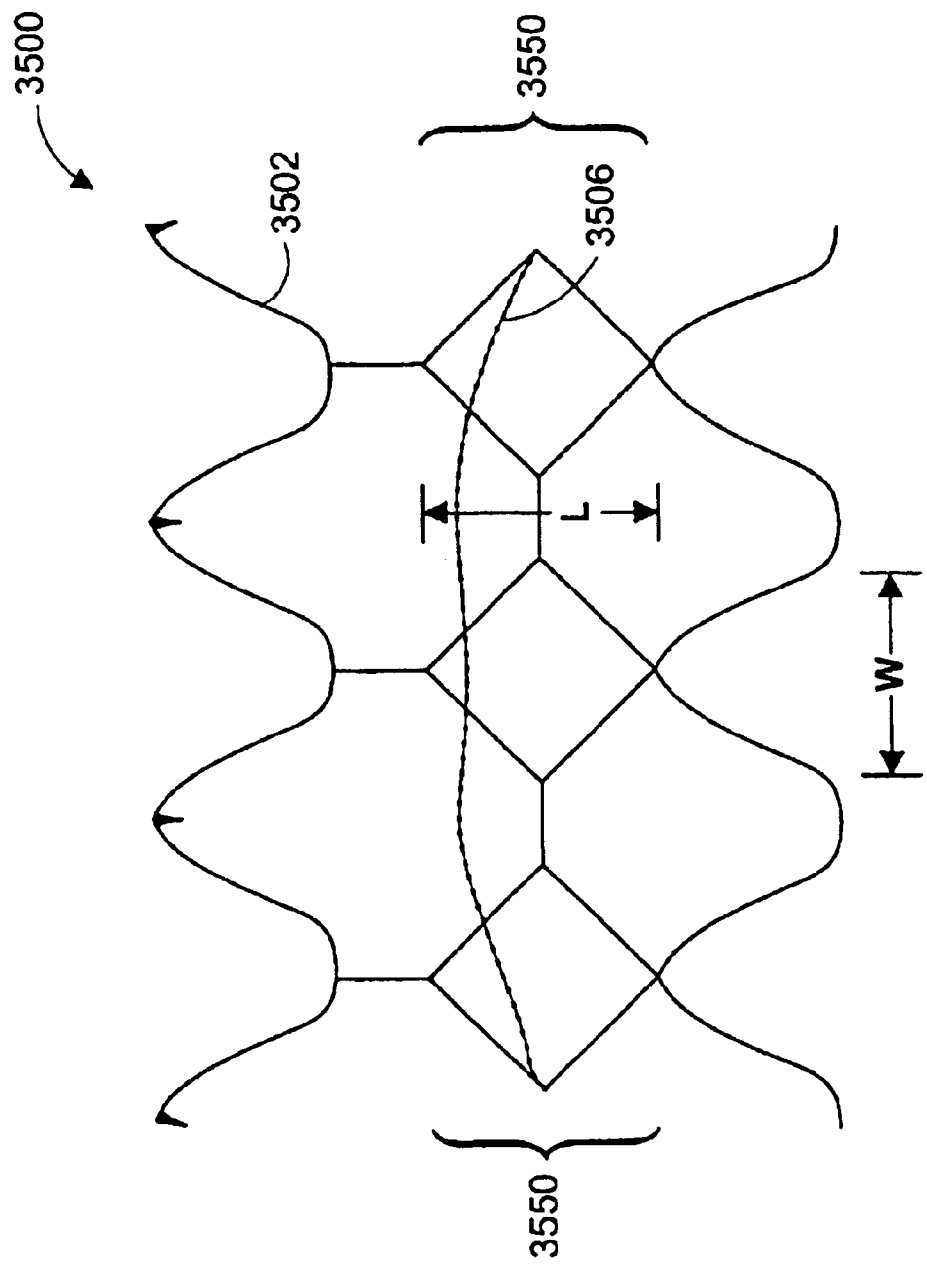
FIG. 35 is a partial elevational view of another occlusion device for occluding a section of a blood vessel in accordance with this invention.

Occlusion plug 3500, which is shown in FIG. 35, is constructed according to this invention, but includes a frame with a different profile from that shown in FIG. 33. FIG. 35 shows a partial view of plug 3500 in the unfurled state. Like each of the other embodiments discussed above, medial portion 3550 can radially expand and axially contract when a balloon is inflated therein. In particular, each of the rectangular units that make up frame 3502 can stretch, such that length l and width w vary inversely.

Figure 36:
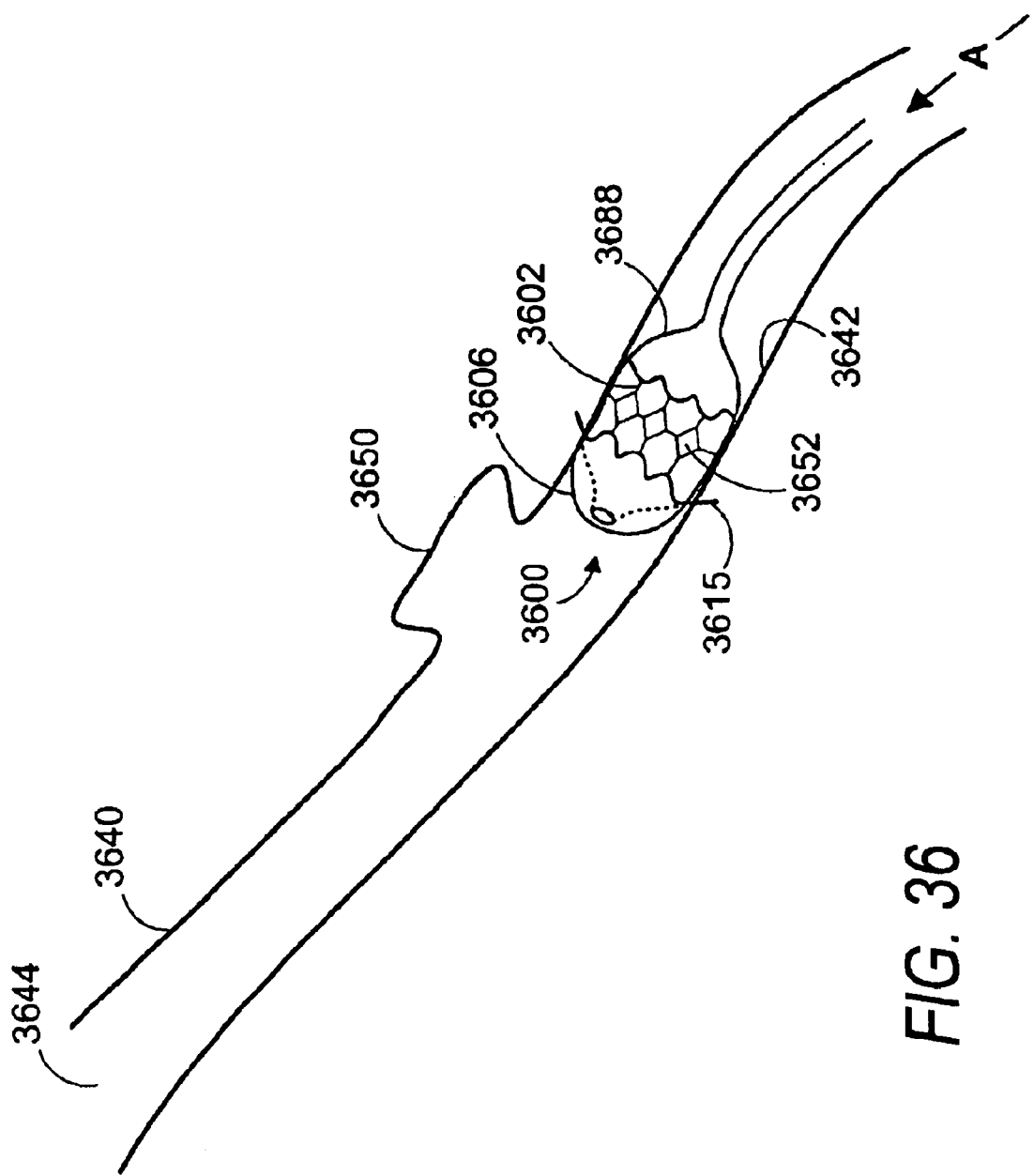
FIG. 36 is a cross-sectional view of the occlusion device shown in FIG. 35 deployed in a blood vessel in accordance with this invention.

FIG. 36 shows the deployment of occlusion plug 3600 in a patient's blood vessel 3640 having aneurysm 3650. Arrow A shows the normal direction of blood flow through blood vessel 3640. Because of aneurysm 3650, it may be desirable to occlude blood vessel 3640 upstream from aneurysm 3650. As already explained above, with reference to plug 2800, for example, plug 3600 is mounted on balloon 3688 and positioned upstream of aneurysm 3650. As balloon 3688 is inflated, perforated tubular portion 3652 expands radially causing perforated tubular portion 3652 to conform to inner wall 3642 of blood vessel 3640. Plugging structure 3606 is attached to frame 3602 at points along the circumference of tubular portion 3652 and is thus stretched to occlude lumen 3644 of blood vessel 3640. As perforated tubular portion 3652 expands radially, it contracts axially and causes piercing points 3615 to engage walls 3642 and thus anchor plug 3600.

It will be understood that the foregoing is only illustrative of the principles of the invention, and that various modifications can be made by those skilled in the art without departing from the scope and spirit of the invention.

What is claimed is:

1. A plug for closing an aperture in a wall of a patient's body cavity, said plug comprising:
    a frame having a central axis comprising:
        a first plurality of fingers configured to engage an interior surface of said wall of said body cavity;
        a second plurality of fingers attached to said first plurality, wherein said second plurality is configured to engage an exterior surface of said wall of said body cavity, and wherein said pluralities of fingers are positioned substantially circumferentially with respect to said axis; and
        a plugging structure that spans said aperture when said plug is inserted in said aperture, wherein said plugging structure is attached to said frame, and wherein any cross-section of said frame that lies in a plane substantially perpendicular to said axis is discontinuous.

2. The plug of claim 1 wherein said plug can be detected using fluoroscopy.

3. The plug of claim 1 wherein said first and second pluralities of fingers are formed from a unitary body.

4. The plug of claim 1 wherein said frame comprises an elastic material.

5. The plug of claim 4 wherein said frame comprises nitinol.

6. The plug of claim 1 wherein at least one finger of at least one of said pluralities of fingers extends substantially radially away from said central axis.

7. The plug of claim 1 wherein at least one finger of at least one of said pluralities of fingers has a marker structure.

8. The plug of claim 7 wherein said marker structure is radiopaque.

9. The plug of claim 7 wherein said marker structure is a marker band.

10. The plug of claim 9 wherein said finger has an end portion and said marker band is crimped to said end portion.

11. The plug of claim 7 wherein said marker structure is a rivet.

12. The plug of claim 1 wherein at least one finger of at least one of said pluralities of fingers has a retention device receptacle.

13. The plug of claim 12 wherein said retention device receptacle is a locking pin aperture.

14. The plug of claim 12 wherein said retention device receptacle is a nose cone cover.

15. The plug of claim 1 wherein at least one finger of at least one of said pluralities of fingers has a pointed end portion located remotely from said central axis.

16. The plug of claim 1 wherein at least one finger of at least one of said pluralities of fingers has a barbed end portion located remotely from said central axis.

17. The plug of claim 1 wherein at least one finger of at least one of said pluralities of fingers is curved, said curve being concave toward a plane perpendicular to said central axis and passing substantially between said first and second pluralities of fingers.

18. The plug of claim 1 wherein said fingers have end portions that are proximal to said central axis and said end portions define a substantially round cross section.

19. The plug of claim 1 wherein said fingers have end portions that are proximal to said central axis and said end portions define a substantially elliptical cross section.

20. The plug of claim 1 wherein substantially all of said fingers of at least one of said pluralities of fingers are of substantially the same length.

21. The plug of claim 1 wherein different fingers of at least one of said pluralities of fingers have different lengths.

22. The plug of claim 1 wherein at least one finger of at least one of said pluralities of fingers has a different flexural stiffness at different points along its length.

23. The plug of claim 1 wherein at least one finger of at least one of said pluralities of fingers has a different thickness at different points along its length.

24. The plug of claim 1 wherein at least one finger of at least one of said pluralities of fingers has a different width at different points along its length.

25. The plug of claim 1 wherein at least one finger of at least one of said pluralities of fingers has a free end portion comprising an end structure configured to facilitate releasable retention of said finger by a plug delivery device.

26. The plug of claim 1 further comprising an elastic web between adjacent ones of said fingers.

27. The plug of claim 26 wherein said web comprises silicone.

28. The plug of claim 1 wherein at least one finger of at least one of said pluralities of fingers has an end portion proximal to said central axis for supporting said plugging structure.

29. The plug of claim 28 wherein said end portions have support structures with which to affix said plugging structure.

30. The plug of claim 1 wherein at least one finger of at least one of said pluralities of fingers has an end portion remote from said central axis for supporting said plugging structure.

31. The plug of claim 30 wherein said end portion has a support structure with which to affix said plugging structure.

32. The plug of claim 1 wherein said plugging structure is elastic.

33. The plug of claim 1 wherein said plugging structure can be unfolded.

34. The plug of claim 1 wherein said plugging structure comprises polymeric material.

35. The plug of claim 1 wherein said plugging structure comprises DACRON®.

36. The plug of claim 1 wherein said plugging structure comprises cloth.

37. The plug of claim 1 wherein said plugging structure is sewn to said frame.

38. The plug of claim 1 wherein said plugging structure has a guide wire aperture through which a guide wire can pass.

39. The plug of claim 38 wherein said guide wire aperture can substantially self close when said guide wire is removed from said guide wire aperture.

40. The plug of claim 1 wherein said frame is insertable into a delivery tube by positioning said fingers in a direction substantially parallel to said central axis.

41. The plug of claim 1 wherein said second plurality of fingers is integral with said first plurality of fingers.

42. The plug of claim 1 wherein said aperture has a perimeter and said frame can conform to said perimeter.

43. A plug comprising:
a perforated tubular portion having a longitudinal passage, wherein any cross-section of said perforated tubular portion in a plane perpendicular to said passage is discontinuous;
a plurality of fingers attached to said tubular portion and extending from an axial end of said perforated tubular portion, wherein any cross-section of said plurality of fingers in a plane perpendicular to said passage is discontinuous; and
a plugging structure substantially occluding said passage.

44. The plug of claim 43 wherein said plug can be detected using fluoroscopy.

45. The plug of claim 43 wherein said perforated tubular portion and said plurality of fingers are formed from a unitary body.

46. The plug of claim 43 further comprising a second plurality of fingers attached to said tubular portion and extending from a second axial end of said perforated tubular portion.

47. The plug of claim 46 wherein said plug can be detected using fluoroscopy.

48. The plug of claim 46 wherein said perforated tubular portion and said first and second pluralities of fingers are formed from a unitary body.

49. The plug of claim 46 wherein said perforated tubular structure and said fingers comprise an elastic material.

50. The plug of claim 49 wherein said perforated tubular structure and said fingers frame comprise nitinol.

51. The plug of claim 46 wherein at least one finger of said pluralities of fingers can be positioned to extend substantially radially away from said longitudinal passage.

52. The plug of claim 46 wherein at least one finger of said plurality of fingers has a marker structure.

53. The plug of claim 52 wherein said marker structure is radiopaque.

54. The plug of claim 52 wherein said marker structure is a marker bands.

55. The plug of claim 54 wherein said finger has an end portion and said marker band is crimped to said end portion.

56. The plug of claim 52 wherein said marker structure is a rivet.

57. The plug of claim 46 wherein at least one finger of at least one of said pluralities of fingers has a retention device receptacle.

58. The plug of claim 57 wherein said retention device receptacle is a locking pin aperture.

59. The plug of claim 58 wherein said retention device receptacle is a nose cone cover.

60. The plug of claim 46 wherein at least one finger of at least one of said pluralities of fingers has a pointed end portion located remotely from said central axis.

61. The plug of claim 46 wherein at least one finger of at least one of said pluralities of fingers has a barbed end portion located remotely from said central axis.

62. The plug of claim 46 wherein at least one finger of at least one of said pluralities of fingers is curved, said curve being concave toward a plane perpendicular to said central axis and passing substantially between said first and second pluralities of fingers.

63. The plug of claim 46 wherein said perforated tubular portion defines a substantially round cross section as viewed in a direction of said longitudinal axis.

64. The plug of claim 46 wherein said perforated tubular portion defines a substantially elliptical cross section as viewed in a direction of said longitudinal passage.

65. The plug of claim 46 wherein substantially all of said fingers of at least one of said pluralities are of substantially similar length.

66. The plug of claim 46 wherein different ones of the fingers of at least one of said pluralities are of different lengths.

67. The plug of claim 46 wherein at least one finger of at least one of said pluralities of fingers has different flexural stiffness along its length.

68. The plug of claim 46 wherein at least one finger of at least one of said pluralities of fingers has different thickness along its length.

69. The plug of claim 46 wherein at least one finger of at least one of said pluralities of fingers has different width along its length.

70. The plug of claim 46 wherein at least one finger of at least one of said pluralities of fingers has a free end portion comprising an end structure configured to facilitate releasable retention of said finger by a plug delivery device.

71. The plug of claim 46 further comprising an elastic web between adjacent ones of said fingers.

72. The plug of claim 71 herein the web comprises silicone.

73. The plug of claim 46 wherein at least one finger of at least one of said pluralities of fingers has an end portion proximal to said central axis for supporting said plugging structure.

74. The plug of claim 46 wherein at least one finger of at least one of said pluralities of fingers has an end portion remote from said central axis for supporting said plugging structure.

75. The plug of claim 74 wherein said end portion has a support structure with which to affix said plugging structure.

76. The plug of claim 46 wherein said perforated tubular portion has at least one support structure with which to affix said plugging structure.

77. The plug of claim 46 wherein said plugging structure is elastic.

78. The plug of claim 46 wherein said plugging structure can be unfolded.

79. The plug of claim 46 wherein said plugging structure comprises polymeric material.

80. The plug of claim 46 wherein said plugging structure comprises DACRON®.

81. The plug of claim 46 wherein said plugging structure comprises cloth.

82. The plug of claim 46 wherein said plugging structure is sewn to said frame.

83. The plug of claim 46 wherein said plugging structure has a guide wire aperture through which a guide wire can pass.

84. The plug of claim 83 wherein said guide wire aperture can substantially self close after said guide wire is removed.

85. The plug of claim 46 wherein said frame may be inserted into a delivery tube by extending said fingers in a direction substantially parallel to said longitudinal passage.

86. The plug of claim 46 wherein said perforated tubular portion can conform to a perimeter of a hole in a wall of a patient's body cavity.

87. The plug of claim 46 wherein said perforated tubular portion can contract longitudinally as it expands radially.

88. The plug of claim 46 wherein said perforated tubular portion is plastically deformable.

89. The plug of claim 88 wherein said perforated tubular portion comprises stainless steel.

90. The plug of claim 89 wherein said tubular portion comprises tantalum.

91. The plug of claim 88 wherein said perforated tubular portion can be conformed to a perimeter of a hole in a wall of a patient's body cavity using a balloon to expand said perforated tubular portion.

92. The plug of claim 88 wherein said perforated tubular portion can contract longitudinally as it expands radially.

93. The plug of claim 43 wherein said perforated tubular portion and said fingers comprise an elastic material.

94. The plug of claim 93 wherein said perforated tubular portion and said fingers comprise nitinol.

95. The plug of claim 43 wherein at least one of said fingers extends substantially radially away from said central axis.

96. The plug of claim 43 wherein at least one of said fingers has a marker structure.

97. The plug of claim 96 wherein said marker structure is radiopaque.

98. The plug of claim 96 wherein said marker structure is a marker band.

99. The plug of claim 98 wherein said finger has an end portion and said marker band is crimped to said end portion.

100. The plug of claim 96 wherein said marker structure is a rivet.

101. The plug of claim 43 wherein at least one of said fingers has a pointed end portion located remotely from said central axis.

102. The plug of claim 43 wherein at least one of said fingers has a barbed end portion located remotely from said central axis.

103. The plug of claim 43 wherein at least one of said fingers is curved, said curve being concave toward a plane perpendicular to said central axis and passing through said perforated tubular portion.

104. The plug of claim 43 wherein said i perforated tubular portion defines a substantially round cross section as viewed in a direction of said longitudinal passage.

105. The plug of claim 43 wherein said perforated tubular portion defines a substantially elliptical cross section as viewed in a direction of said longitudinal passage.

106. The plug of claim 43 wherein substantially all of said fingers are of substantially similar length.

107. The plug of claim 43 wherein different ones of the fingers are of different lengths.

108. The plug of claim 43 wherein at least one of said fingers has different flexural stiffness along its length.

109. The plug of claim 43 wherein at least one of said fingers has different thickness along its length.

110. The plug of claim 43 wherein at least one of said fingers has different width along its length.

111. The plug of claim 43 wherein at least one of said fingers has a free end portion comprising an end structure configured to facilitate releasable retention of said finger by a plug delivery device.

112. The plug of claim 43 further comprising an elastic web between adjacent ones of said fingers.

113. The plug of claim 112 wherein the web comprises silicone.

114. The plug of claim 43 wherein at least one of said fingers has an end portion proximal to said central axis for supporting said plugging structure.

115. The plug of claim 114 wherein said end portion has a support structure with which to affix said plugging structure.

116. The plug of claim 43 wherein said perforated tubular portion has at least one support structure for supporting said plugging structure.

117. The plug of claim 43 wherein said plugging structure is elastic.

118. The plug of claim 43 wherein said plugging structure can be unfolded.

119. The plug of claim 43 wherein said plugging structure comprises polymeric material.

120. The plug of claim 43 wherein said plugging structure comprises DACRON®.

121. The plug of claim 43 wherein said plugging structure comprises cloth.

122. The plug of claim 43 wherein said plugging structure is sewn to said frame.

123. The plug of claim 43 wherein said plugging structure has a guide wire aperture through which a guide wire can pass.

124. The plug of claim 123 wherein said guide wire aperture can substantially self close after said guide wire is removed.

125. The plug of claim 43 wherein said frame may be inserted into a delivery tube by extending said fingers in a direction substantially parallel to said longitudinal passage.

126. The plug of claim 43 wherein said perforated tubular portion can conform to a perimeter of a defect in a wall of a patient's body cavity.

127. The plug of claim 43 wherein said perforated tubular portion can contract longitudinally as it expands radially.

128. The plug of claim 43 wherein said perforated tubular portion is plastically deformable.

129. The plug of claim 128 wherein said perforated tubular portion comprises stainless steel.

130. The plug of claim 128 wherein said perforated tubular portion comprises tantalum.

131. The plug of claim 128 wherein said perforated tubular portion can be conformed to a perimeter of a hole in a wall of a patient's body cavity using a balloon to expand said perforated tubular portion.

132. The plug of claim 128 wherein said perforated tubular portion can contract longitudinally as it expands radially.

133. A method for plugging an aperture in a wall of a patient's body cavity comprising:
positioning in said aperture a conformable plug having a first plurality of fingers, a second plurality of fingers, and a central axis, wherein said pluralities are arranged about said axis at opposite axial ends, and wherein said plug also has a plugging structure;
conforming said plug to said aperture; and
securing said plug in said aperture.

134. The method of claim 133 wherein said positioning comprises locating said plug using fluoroscopy.

135. The method of claim 133 wherein said positioning comprises providing a delivery structure for installing said plug.

136. The method of claim 135 wherein said positioning further comprises:
extending said fingers in a direction substantially parallel to said central axis; and
inserting said plug into a sleeve.

137. The method of claim 136 wherein said positioning further comprises engaging at least one of said fingers with a locking pin.

138. The method of claim 137 wherein said positioning further comprises releasing at least one finger from a locking pin.

139. The method of claim 135 wherein said positioning further comprises inserting said delivery structure through an insertion aperture in a patient's body tissue.

140. The method of claim 135 wherein said positioning further comprises shifting said delivery structure relative to said plug and said aperture so that (1) said delivery structure is removed from said aperture but said plug extends through said aperture; (2) said fingers extend out from said axis, wherein each of said first and second pluralities on opposite sides of said wall; and (3) said plugging structure substantially occludes said aperture.

141. The method of claim 140 wherein said positioning further comprises allowing said fingers to engage said respective opposite sides of said wall.

142. The method of claim 140 wherein said conforming comprises allowing said plug to elastically expand in said aperture until said plug substantially conforms to a perimeter of said aperture.

143. The method of claim 140 wherein said positioning further comprises allowing said plug to elastically contract longitudinally to cause said fingers to engage said respective opposite sides of said wall.

144. The method of claim 143 wherein said allowing further comprises allowing said plug to substantially center itself with respect to said wall in a direction along said longitudinal passage.

145. A method for occluding blood flow in a tube of a patient's circulatory system, said method comprising:
positioning in said tube a conformable plug having a first plurality of fingers, a tubular portion, a plugging structure, and a central axis, wherein said plurality of fingers is arranged circumferentially about said central axis and wherein said plugging structure spans across said tubular portion;
conforming said plug to said tube; and
securing said plug in said tube.

146. The method of claim 145 wherein said positioning comprises locating said plug using fluoroscopy.

147. The method of claim 145 wherein said positioning comprises providing a delivery balloon for installing said plug.

148. The method of claim 145 wherein said positioning further comprises:
inserting said delivery balloon in said tubular portion; and
delivering said plug through the patient's body tissue to said tube.

149. The method of claim 148 wherein said delivering further comprises inserting said balloon and said plug through an insertion aperture in a patient's body tissue.

150. The method of claim 148 wherein said positioning further comprises moving said plug mounted on said balloon through a patient's existing body tubing so that said plug is positioned in said tube at a desired location.

151. The method of claim 150 wherein said conforming comprises:
expanding said balloon; and
radially enlarging said tubular portion until said tubular portion until said plurality of fingers engages with an inside surface of said tube, wherein said plugging structure substantially occludes said tube.

152. The method of claim 151 wherein said enlarging comprises plastically deforming said plug.

153. The method of claim 151 wherein said positioning further comprises allowing said plug to substantially center itself with respect to said wall in a direction along said longitudinal passage.

* * * * *